(12) United States Patent
Yano et al.

(10) Patent No.: US 9,588,076 B2
(45) Date of Patent: Mar. 7, 2017

(54) BIOSENSOR AND METHOD FOR MANUFACTURING BIOSENSOR

(71) Applicant: Panasonic Healthcare Holdings Co., Ltd., Tokyo (JP)

(72) Inventors: Setuko Yano, Ehime (JP); Kazumasa Miyamoto, Ehime (JP); Shinki Kojima, Ehime (JP); Tomoharu Yamamura, Ehime (JP); Kanako Matsushima, Ehime (JP)

(73) Assignee: Panasonic Healthcare Holdings Co., Ltd., Tokyo (JP)

( * ) Notice: Subject to any disclaimer, the term of this patent is extended or adjusted under 35 U.S.C. 154(b) by 0 days.

(21) Appl. No.: 14/426,642

(22) PCT Filed: Sep. 19, 2013

(86) PCT No.: PCT/JP2013/005542
§ 371 (c)(1),
(2) Date: Mar. 6, 2015

(87) PCT Pub. No.: WO2014/045584
PCT Pub. Date: Mar. 27, 2014

(65) Prior Publication Data
US 2015/0241377 A1   Aug. 27, 2015

(30) Foreign Application Priority Data

Sep. 19, 2012   (JP) .................................. 2012-205274

(51) Int. Cl.
*G01N 27/327* (2006.01)
*C12Q 1/00* (2006.01)

(52) U.S. Cl.
CPC ......... *G01N 27/3271* (2013.01); *C12Q 1/006* (2013.01); *G01N 27/3272* (2013.01)

(58) Field of Classification Search
CPC ........... G01N 27/3271; G01N 27/3272; G01N 27/48; G01N 27/26; A61B 5/05;
(Continued)

(56) References Cited

U.S. PATENT DOCUMENTS 5,126,247 A * 6/1992 Palmer .................... C12Q 1/26
435/174
8,210,349 B2   7/2012 Yamaoka
(Continued)

FOREIGN PATENT DOCUMENTS

CN     1764832     4/2006
CN     1842705    10/2006
(Continued)

OTHER PUBLICATIONS

Zhang et al., Colloids and Surfaces B:Biointerfaces 74,200928-31.*
(Continued)

*Primary Examiner* — Gurpreet Kaur
(74) *Attorney, Agent, or Firm* — Hamre, Schumann, Mueller & Larson, P.C.

(57) ABSTRACT

The present invention relates to a biosensor, and it is an object thereof to suppress degradation by light. A biosensor (2) comprises a blood component measurement working electrode (5), a blood component measurement counter electrode (6), and a reagent component (9). The reagent component (9) is provided near the blood component measurement working electrode (5) and the blood component measurement counter electrode (6). The reagent component (9) includes a mediator, an oxidoreductase, and a substance that absorbs light with a wavelength of 400 to 500 nm. An insulated substrate (4) is provided, on the surface of which is disposed the blood component measurement working electrode (5) and/or the blood component measurement
(Continued)

counter electrode (6). The reagent component (9) is disposed on the one or more electrodes on the insulated substrate (4).

16 Claims, 17 Drawing Sheets

(58) Field of Classification Search
 CPC  A61B 5/14532; A61B 5/150358; C12Q 1/00; C12Q 1/001; C12Q 1/003; C12Q 1/004; C12Q 1/006; C12Q 1/02; C12Q 1/34; C12Q 1/54
 See application file for complete search history.

(56) References Cited

U.S. PATENT DOCUMENTS

| | | |
|---|---|---|
| 2005/0008537 A1 | 1/2005 | Mosoiu et al. |
| 2005/0013731 A1 | 1/2005 | Burket et al. |
| 2005/0016844 A1 | 1/2005 | Burket et al. |
| 2006/0191813 A1 | 8/2006 | Yamaoka |
| 2007/0235346 A1* | 10/2007 | Popovich ............... C12Q 1/004 205/777.5 |
| 2007/0295616 A1 | 12/2007 | Harding et al. |
| 2009/0151864 A1 | 6/2009 | Burket et al. |
| 2009/0162532 A1 | 6/2009 | Mosoiu et al. |
| 2009/0255811 A1* | 10/2009 | Forrow ................. C12Q 1/001 204/403.14 |
| 2011/0000610 A1 | 1/2011 | Burke et al. |
| 2011/0011738 A1 | 1/2011 | Burke et al. |
| 2011/0046466 A1* | 2/2011 | Feldman ............... A61B 5/1486 600/347 |
| 2011/0174618 A1 | 7/2011 | Bryan |
| 2012/0009095 A1 | 1/2012 | Burke et al. |
| 2012/0150005 A1* | 6/2012 | Hoss .................. A61B 5/14532 600/347 |

FOREIGN PATENT DOCUMENTS

| | | |
|---|---|---|
| EP | 1628129 | 2/2006 |
| JP | 2006-170631 | 6/2006 |
| JP | 2009-210347 | 9/2009 |
| JP | 2012-504233 | 2/2012 |
| WO | WO 2004/092720 | 10/2004 |
| WO | WO 2010/092720 | 10/2004 |
| WO | 2004113901 | 12/2004 |

OTHER PUBLICATIONS

PUbChem Brilliant Blue FCF.*
PUbChem Fast Green FCF.*
International Search Report Dec. 24, 2013; PCT/JP2013/005542 (1 page).
Extended European Search Report issued in the corresponding European application No. EP13839044, dated Sep. 18, 2015, 8 pages.
Dekker et al., "Covalent Addition of H2O, Enzymes Substrates and Activators to Pyrrolo-quinoline Quinone, the Coenzyme of Quinoproteins", Eur. J. Biochem., vol. 125, pp. 69-73, Mar. 29, 1982.
Office Action from the Chinese Patent Application No. 201380048522.2, issued on Mar. 1, 2016, 13 pages.

* cited by examiner

| Substance name | | Wavelength λ | Absorbancy Abs | Molar concentration c (M) | Molar extinction coefficient ε | ε (PQSA) ratio |
|---|---|---|---|---|---|---|
| PQSA | | 414 | 0.212 | 0.0001 | 2120 | 1.000 |
| Food Green No. 3 | Fast Green FCF | 408 | 0.128 | 0.0001 | 12800 | 6.038 |
| Food Blue No. 1 | Brilliant Blue FCF | 414 | 1.550 | 0.0001 | 15500 | 7.311 |
| Food Yellow No. 4 | tartrazine | 414 | 0.274 | 0.00001 | 27400 | 12.925 |

FIG. 10

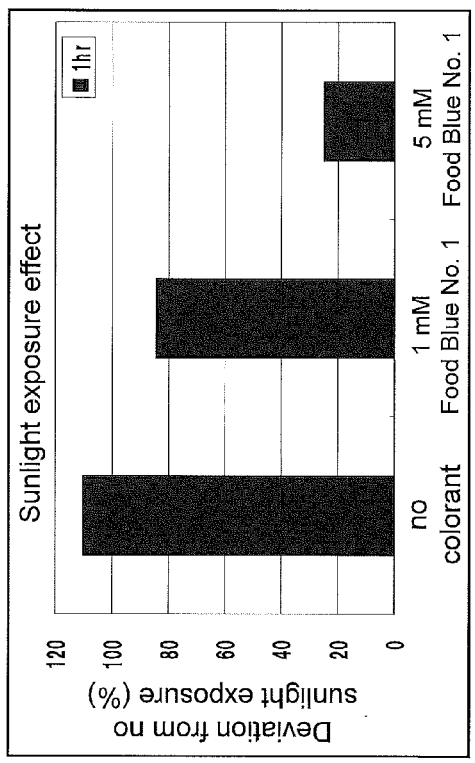
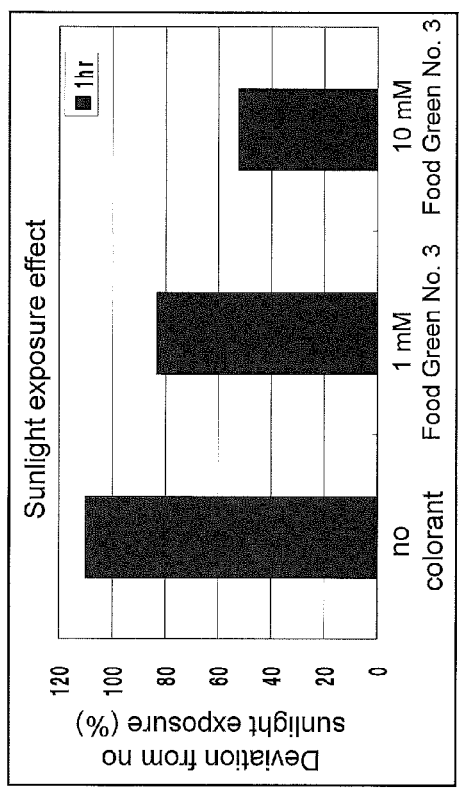
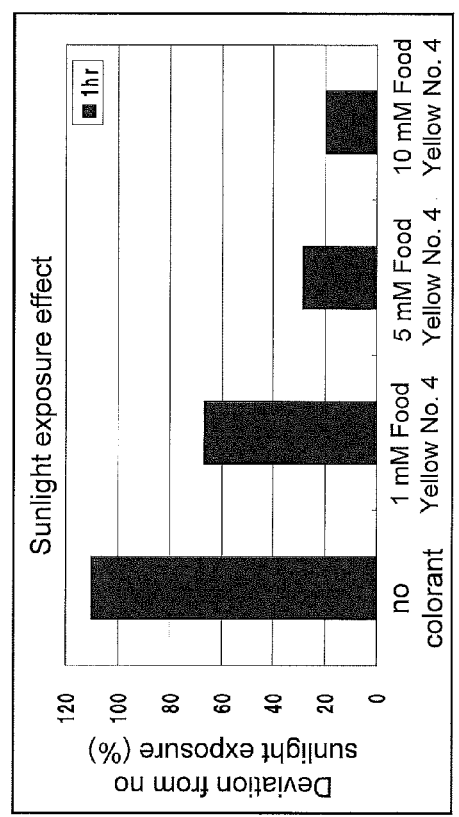
FIG. 13

(a)

| Reagent | Molar concentration (mM) | Concentration | |
|---|---|---|---|
| | | Solution | Dry |
| enzyme | | 7.41% | 4U/cell |
| Food Green No. 3 (Mw 808.87) | 1.00 | 0.08% | 6.01% |
| $K_2HPO_4$ | | 0.05% | 3.96% |
| $KH_2PO_4$ | | 0.04% | 3.02% |
| $NaH_2PO_4$ | | 0.11% | 8.03% |
| CMC | | 0.13% | 9.29% |
| ATA | | 0.04% | 3.12% |
| maltitol | | 0.17% | 12.81% |
| PQSA | 22.6 | 0.70% | 51.89% |
| Other components | | 0.03% | 1.86% |
| water | | 91.25% | |
| Total | | 100% | 100% |

(b)

| Reagent | Molar concentration (mM) | Concentration | |
|---|---|---|---|
| | | Solution | Dry |
| enzyme | | 7.41% | 4U/cell |
| Food Green No. 3 (Mw 808.87) | 10.00 | 0.81% | 39.02% |
| $K_2HPO_4$ | | 0.05% | 2.57% |
| $KH_2PO_4$ | | 0.04% | 1.96% |
| $NaH_2PO_4$ | | 0.11% | 5.21% |
| CMC | | 0.13% | 6.03% |
| ATA | | 0.04% | 2.03% |
| maltitol | | 0.17% | 8.31% |
| PQSA | 22.6 | 0.70% | 33.67% |
| Other components | | 0.03% | 1.21% |
| water | | 91.25% | |
| Total | | 101% | 100% |

| Reagent | Molar concentration (mM) | Concentration | |
|---|---|---|---|
| | | Solution | Dry |
| enzyme | | 7.41% | 4U/cell |
| Food Blue No. 1 (Mw 792.86) | 1.00 | 0.08% | 5.90% |
| K$_2$HPO$_4$ | | 0.05% | 3.97% |
| KH$_2$PO$_4$ | | 0.04% | 3.03% |
| NaH$_2$PO$_4$ | | 0.11% | 8.04% |
| CMC | | 0.13% | 9.30% |
| ATA | | 0.04% | 3.13% |
| maltitol | | 0.17% | 12.83% |
| PQSA | 22.6 | 0.70% | 51.95% |
| Other components | | 0.03% | 1.86% |
| water | | 91.25% | |
| Total | | 100% | 100% |

(b)

| Reagent | Molar concentration (mM) | Concentration | |
|---|---|---|---|
| | | Solution | Dry |
| enzyme | | 7.41% | 4U/cell |
| Food Blue No. 1 (Mw 792.86) | 5.00 | 0.40% | 23.87% |
| K$_2$HPO$_4$ | | 0.05% | 3.21% |
| KH$_2$PO$_4$ | | 0.04% | 2.45% |
| NaH$_2$PO$_4$ | | 0.11% | 6.50% |
| CMC | | 0.13% | 7.53% |
| ATA | | 0.04% | 2.53% |
| maltitol | | 0.17% | 10.38% |
| PQSA | 22.6 | 0.70% | 42.03% |
| Other components | | 0.03% | 1.51% |
| water | | 91.25% | |
| Total | | 101% | 100% |

| Reagent | Molar concentration (mM) | Concentration | |
|---|---|---|---|
| | | Solution | Dry |
| enzyme | | 7.41% | 4U/cell |
| Food Yellow No. 4 (Mw 534.37) | 1.00 | 0.05% | 4.06% |
| $K_2HPO_4$ | | 0.05% | 4.05% |
| $KH_2PO_4$ | | 0.04% | 3.09% |
| $NaH_2PO_4$ | | 0.11% | 8.20% |
| CMC | | 0.13% | 9.49% |
| ATA | | 0.04% | 3.19% |
| maltitol | | 0.17% | 13.08% |
| PQSA | 22.6 | 0.70% | 52.97% |
| Other components | | 0.03% | 1.90% |
| water | | 91.27% | |
| Total | | 100% | 100% |

(b)

| Reagent | Molar concentration (mM) | Concentration | |
|---|---|---|---|
| | | Solution | Dry |
| enzyme | | 7.41% | 4U/cell |
| Food Yellow No. 4 (Mw 534.37) | 5.00 | 0.27% | 17.45% |
| $K_2HPO_4$ | | 0.05% | 3.48% |
| $KH_2PO_4$ | | 0.04% | 2.66% |
| $NaH_2PO_4$ | | 0.11% | 7.05% |
| CMC | | 0.13% | 8.16% |
| ATA | | 0.04% | 2.74% |
| maltitol | | 0.17% | 11.25% |
| PQSA | 22.6 | 0.70% | 45.58% |
| Other components | | 0.03% | 1.63% |
| water | | 91.27% | |
| Total | | 100% | 100% |

(c)

| Reagent | Molar concentration (mM) | Concentration | |
|---|---|---|---|
| | | Solution | Dry |
| enzyme | | 7.41% | 4U/cell |
| Food Yellow No. 4 (Mw 534.37) | 10.00 | 0.53% | 29.71% |
| $K_2HPO_4$ | | 0.05% | 2.97% |
| $KH_2PO_4$ | | 0.04% | 2.26% |
| $NaH_2PO_4$ | | 0.11% | 6.00% |
| CMC | | 0.13% | 6.95% |
| ATA | | 0.04% | 2.34% |
| maltitol | | 0.17% | 9.58% |
| PQSA | 22.6 | 0.70% | 38.81% |
| Other components | | 0.03% | 1.39% |
| water | | 91.27% | |
| Total | | 100% | 100% |

FIG. 16

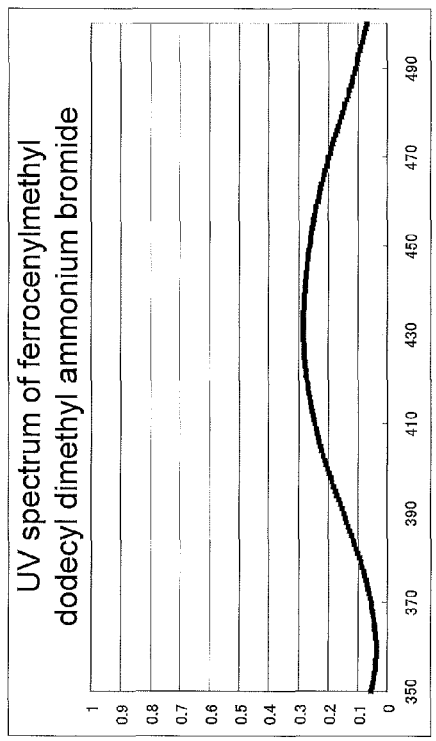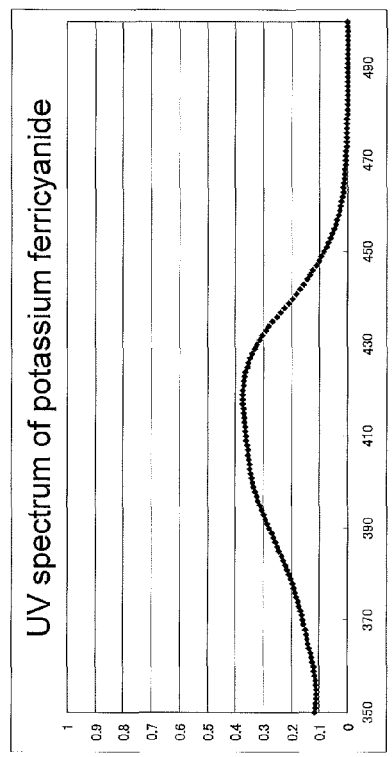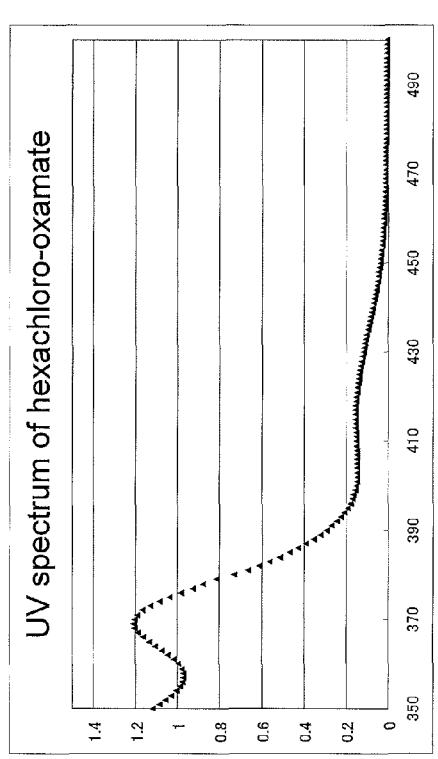
FIG. 17

BIOSENSOR AND METHOD FOR MANUFACTURING BIOSENSOR

TECHNICAL FIELD

The present invention relates to a biosensor for measuring blood glucose levels, for example, and to a method for manufacturing this biosensor.

BACKGROUND ART

A biosensor of this type was configured as follows in the past.

Specifically, there are provided a reagent and first and second electrodes that become conductive via this reagent when a biological sample is supplied to the reagent, and the reagent comprises a mediator, an oxidoreductase, and an adhesive agent.

That is, when a biological sample is supplied to the reagent, the biological sample and the oxidoreductase react, the mediator transmits the electrons produced by this reaction, and the redox current flowing between the first and second electrodes at this point is measured to find a blood glucose level.

The reagent (and particularly the mediator) is known to be affected by light (visible light) and to affect measurement accuracy. Therefore, there were attempts in the past to provide a light effect reducing agent to the walls of the holding container holding the biosensor (see Patent Literature 1, for example).

CITATION LIST

Patent Literature

Patent Literature 1: International Laid-Open Patent Application 2004/092720

SUMMARY

Technical Problem

In the conventional example above, because the light effect reducing agent was provided to the walls of the holding container holding the biosensor, degradation of the biosensor could be prevented in a state in which the biosensor was held in the container. Once the biosensor was removed from the container, however, it was immediately affected by light. Naturally, this effect is only minimal if a biosensor is used right away after being removed from its container, but if the biosensor is left out for a long time before being used, it can degrade. Also, the many other biosensors held in the container are affected by light every time a biosensor is taken out, and this also contributes to degradation.

In view of this, it is an object of the present invention to reduce the degradation of a biosensor by light.

Solution to Problem

To achieve this object, the present invention comprises a first electrode, a second electrode, and a reagent component. The reagent component is provided near the first electrode and the second electrode. The reagent component includes a mediator, an oxidoreductase, and a substance that absorbs light with a wavelength of 400 to 500 nm.

The present invention also comprises a first electrode, a second electrode, and a reagent component. The reagent component includes a mediator, an oxidoreductase, and a light effect reducing agent that reduces the effect of light on the mediator.

Adventageous Effects

The present invention provides a biosensor with which there is less degradation by light, as well as a method for manufacturing this biosensor.

BRIEF DESCRIPTION OF DRAWINGS

FIG. 10 is a table of the maximum absorption wavelengths (nm) of Food Blue No. 1, Food Green No. 3, and Food Yellow No. 4, the absorbancy (Abs) of these wavelengths, the concentration (M) at which this absorbancy is exhibited, the molar extinction coefficient ($\epsilon$), and the ratio of the molar extinction coefficient to PQSA, which is an example of a mediator, along with the PQSA;

FIG. 13a is a graph of the sunlight exposure effect when using Food Green No. 3, FIG. 13b is a graph of the sunlight exposure effect when using Food Blue No. 1, and FIG. 13c is a graph of the sunlight exposure effect when using Food Yellow No. 4;

FIGS. 14a and 14b are tables of the compositions of the reagent component and the reagent solution when using Food Green No. 3;

FIGS. 15a and 15b are tables of the compositions of the reagent component and the reagent solution when using Food Blue No. 1;

FIGS. 16a and 16b are tables of the compositions of the reagent component and the reagent solution when using Food Yellow No. 4; and FIGS. 17a to 17c are graphs of the absorption spectra of other mediators.

DESCRIPTION OF EMBODIMENTS

Embodiments of the present invention will now be described through reference to the appended drawings.

Embodiment 1

The biological sample measurement system 100 in an embodiment pertaining to the present invention will now be described.

Overview of Biological Sample Measurement System 100

Figure 1:
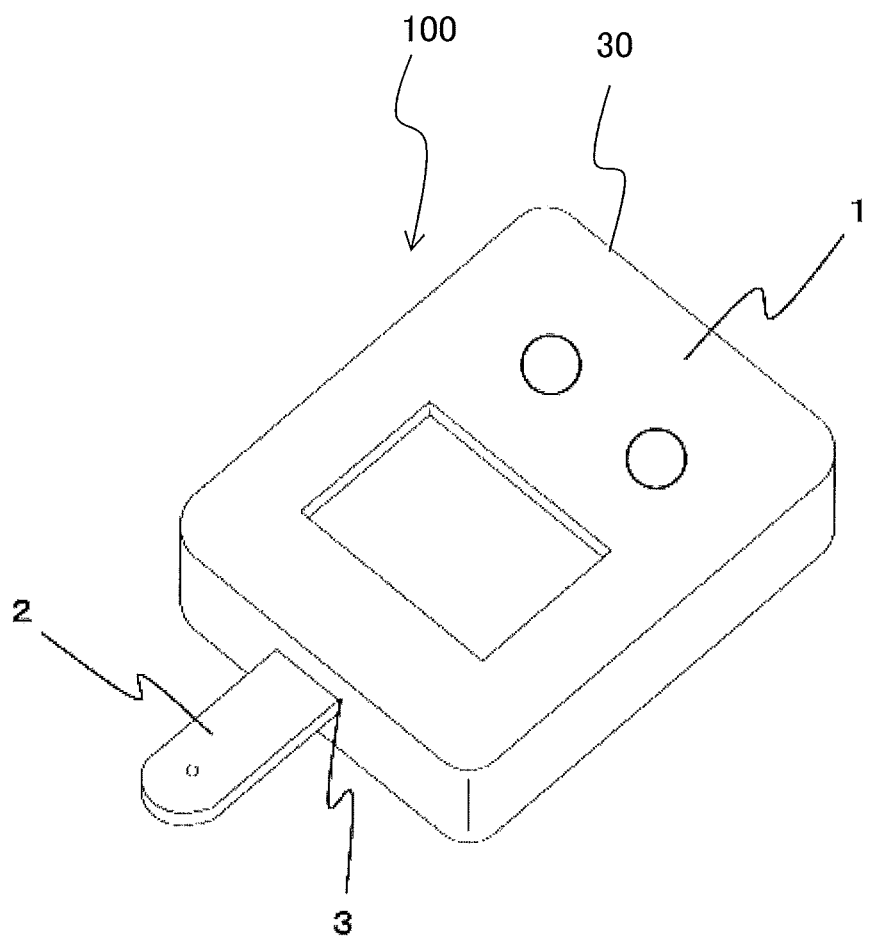
FIG. 1 is an oblique view of a biological sample measurement system when the biosensor pertaining to an embodiment of the present invention has been mounted in a measurement device.

As shown in FIG. 1, the biological sample measurement system 100 in this embodiment comprises a biosensor 2 and a measurement device 30.

Figure 2:
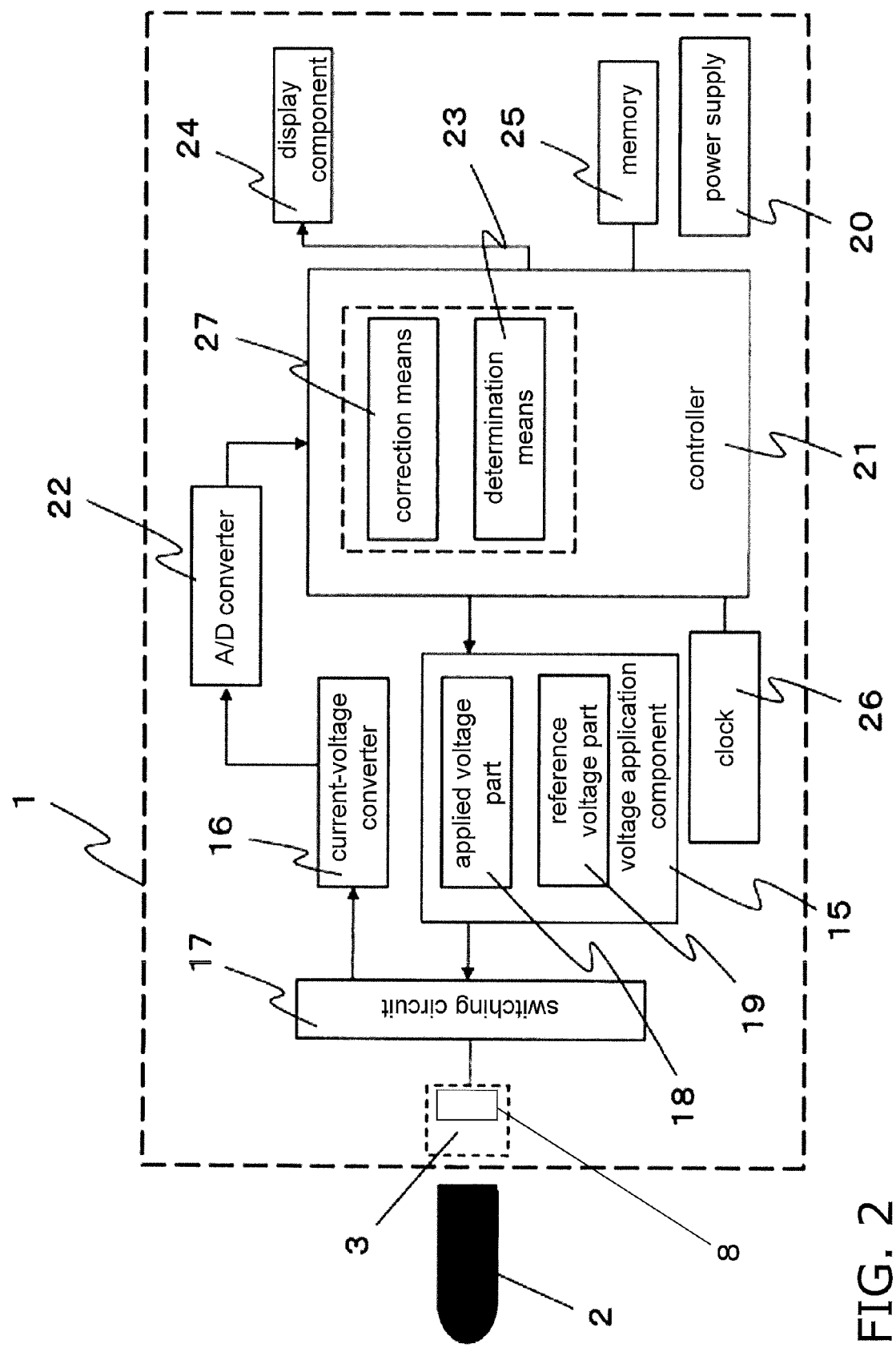
FIG. 2 is a control block diagram of the biological sample measurement system in FIG. 1.

An embodiment of the present invention is shown in FIGS. 1 and 2, in which an insertion slot 3 for the biosensor 2 is provided at one end of a main case 1 constituting the measurement device 30.

Biosensor 2

Figure 3:
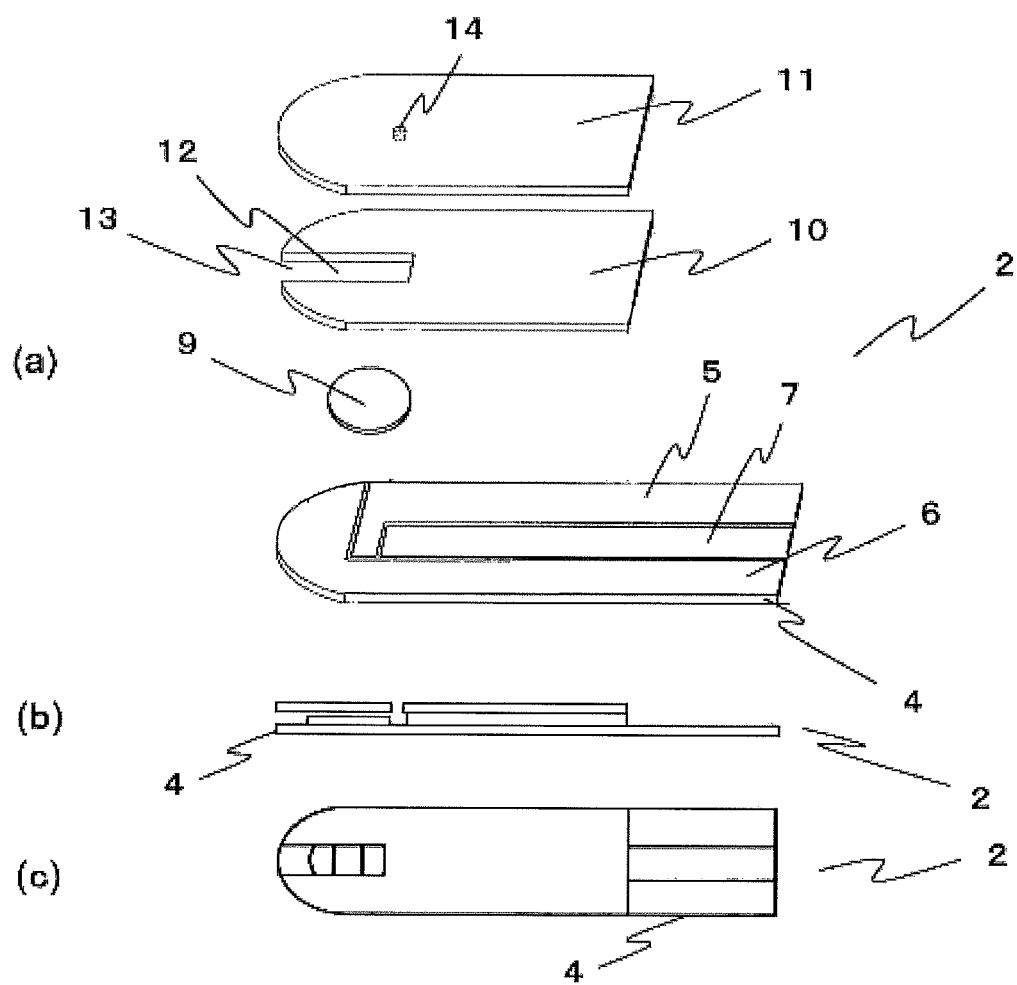
FIG. 3a is an exploded oblique view of the biosensor in FIG. 1.
FIG. 3b is a front view of the biosensor in FIG. 1.
FIG. 3c is a plan view of the biosensor in FIG. 1.

As shown in FIG. 3, the biosensor 2 is provided with three electrodes on a rectangular insulated substrate 4. The three electrodes are a blood component measurement working electrode 5 (an example of a first electrode), a blood component measurement counter electrode 6 (an example of a second electrode), and a blood component detection electrode 7 (an example of a third electrode). These are disposed opposite each other and spaced a specific distance apart.

The blood component measurement working electrode 5, the blood component measurement counter electrode 6, and the blood component detection electrode 7 at one end of the insulated substrate 4 (see the right side in FIG. 3a) are inserted through the insertion slot 3 shown in FIG. 1 into the main case 1, and are brought into contact with an input terminal component 8 (see FIG. 2) and thereby electrically connected to the measurement device.

As shown in FIG. 3, at the other end of the biosensor 2 (the opposite side from the part inserted into the insertion slot 3), a reagent component 9 is disposed over the blood component measurement working electrode 5, the blood component measurement counter electrode 6, and the blood component detection electrode 7.

In this state, the blood component measurement working electrode 5, the blood component measurement counter electrode 6, and the blood component detection electrode 7 are connected via the reagent component 9. The reagent component 9 includes glucose dehydrogenase or another such oxidoreductase, a mediator, and a light effect reducing agent, and also selectively includes a buffer, a polymeric material, an enzyme stabilizer, a crystal homogenizer, or the like as optional components.

As shown in FIGS. 3a to 3c, a cover 11 is disposed via a spacer 10 over the insulated substrate 4 and the reagent component 9. However, at one end of the insulated substrate 4 (the right side in FIG. 3), the blood component measurement working electrode 5, the blood component measurement counter electrode 6, and the blood component detection electrode 7 are exposed, without being covered by the spacer 10 and the cover 11.

The biosensor 2 and the measurement device are configured so that the exposed blood component measurement working electrode 5, blood component measurement counter electrode 6, the blood component detection electrode 7 are electrically connected to the input terminal component 8.

As shown in FIG. 3, a biological sample introduction path 12 for introducing blood is formed in the spacer 10 of the biosensor 2. This biological sample introduction path 12 extends from the other end side of the biosensor 2 (the left side in FIG. 3) to above the reagent component 9, and the other end side that opens to the outside serves as a blood supply opening 13 (also called a biological sample supply opening). Specifically, a biological sample deposited in this blood supply opening 13 moves under capillary action along the biological sample introduction path 12 and reaches the reagent component 9.

As discussed above, the blood component measurement working electrode 5, the blood component measurement counter electrode 6, and the blood component detection electrode 7 are electrically connected to the input terminal component 8, and more specifically, the blood component measurement working electrode 5 is connected to a first input terminal (not shown) of the input terminal component 8, the blood component measurement counter electrode 6 is connected to a second input terminal (not shown) of the input terminal component 8, and the blood component detection electrode 7 is connected to a third input terminal (not shown) of the input terminal component 8.

As can be understood from FIG. 3, the blood component measurement counter electrode 6 is the one disposed closest to the blood supply opening 13, then the blood component measurement working electrode 5, and finally the blood component detection electrode 7.

That is, the blood component measurement counter electrode 6 (an example of a second electrode), the blood component measurement working electrode 5 (an example of a first electrode), and the blood component detection electrode 7 (an example of a third electrode) are disposed in that order starting from the blood supply opening 13 side.

An air hole 14 is formed in the cover 11 of the biosensor 2 to promote capillary action when blood is deposited in the blood supply opening 13 and to cause the blood to penetrate all the way to the portion of the blood component measurement counter electrode 6 that goes beyond the blood component measurement working electrode 5 (the blood component detection electrode 7).

The configuration of the biosensor 2 will now be described in further detail.

Insulated Substrate 4

There are no particular restrictions on the material of the insulated substrate 4, but examples include polyethylene terephthalate (PET), polycarbonate (PC), polyimide (PI), polyethylene (PE), polypropylene (PP), polystyrene (PS), polyvinyl chloride (PVC), polyoxymethylene (POM), monomer-cast nylon (MC), polybutylene terephthalate (PBT), polymethyl methacrylate (PMMA), ABS resin (ABS), and glass. Among these, polyethylene terephthalate (PET), polycarbonate (PC), and polyimide (PI) are preferable, and polyethylene terephthalate (PET) is more preferable.

There are no particular restrictions on the size of the insulated substrate 4, but examples include an overall length of 5 to 100 mm, a width of 2 to 50 mm, and a thickness of 0.05 to 2 mm; preferably, the overall length is 7 to 50 mm, the width is 3 to 20 mm, and the thickness is 0.1 to 1 mm; and more preferably the overall length is 10 to 30 mm, the width is 3 mm to 10 mm, and the thickness is 0.1 mm to 0.6 mm.

The electrodes on the insulated substrate 4 can be formed, for example, by forming a conductive layer of gold, platinum, palladium, or the like by sputtering or vapor deposition, and then working the conductive layer into a particular electrode pattern with a laser. Examples of the laser include YAG lasers, $CO_2$ lasers, and excimer lasers. The electrode pattern is not limited to what is disclosed in the present invention, and any configuration can be used as long as it allows the effects discussed in the present invention to be realized. Covering the surface of the electrodes can be accomplished, for example, by preparing a solution of a polymer material, applying this to the electrode surface by coating or dropping, and then drying. The drying can be accomplished, for example, by natural drying, forced air drying, hot air drying, heat drying, or the like.

Reagent Component 9

As discussed above, the reagent component 9 includes glucose dehydrogenase or another such oxidoreductase, a mediator, and a light effect reducing agent, and also selectively includes a buffer, a polymeric material, an enzyme stabilizer, a crystal homogenizer, or the like as optional components.

When the reagent solution used to form the reagent component 9 is prepared using water, the water will be contained in the largest amount. In terms of the number of moles, the mediator is contained in the largest amount in the water, and there is less light effect reducing agent than mediator.

The water evaporates from the dried reagent component 9. Accordingly, in terms of the number of moles, the mediator is contained in the largest amount, and there is less light effect reducing agent than mediator.

Mediator

There are no particular restrictions on the mediator of the biosensor 2, but examples include ferricyanides, p-benzoquinone, p-benzoquinone derivatives, phenazine methosulfate, methylene blue, ferrocene, ferrocene derivatives, and phenothiazine and its derivatives.

A quinone compound is a compound containing a quinone. Quinone compounds include quinone and quinone derivatives. Examples of quinone derivatives include compounds to which various functional groups (which may also be called substituents) have been added to quinone.

Examples of the quinone in a quinone compound include benzoquinone, naphthoquinone, anthraquinone, phenanthrenequinone, and phenanthroline quinone. A specific example of a phenanthrenequinone is 9,10-phenanthrenequinone. More specifically, examples include sodium 9,10-phenanthrenequinone-2-sulfonate (hereinafter, PQSA).

Figure 11:
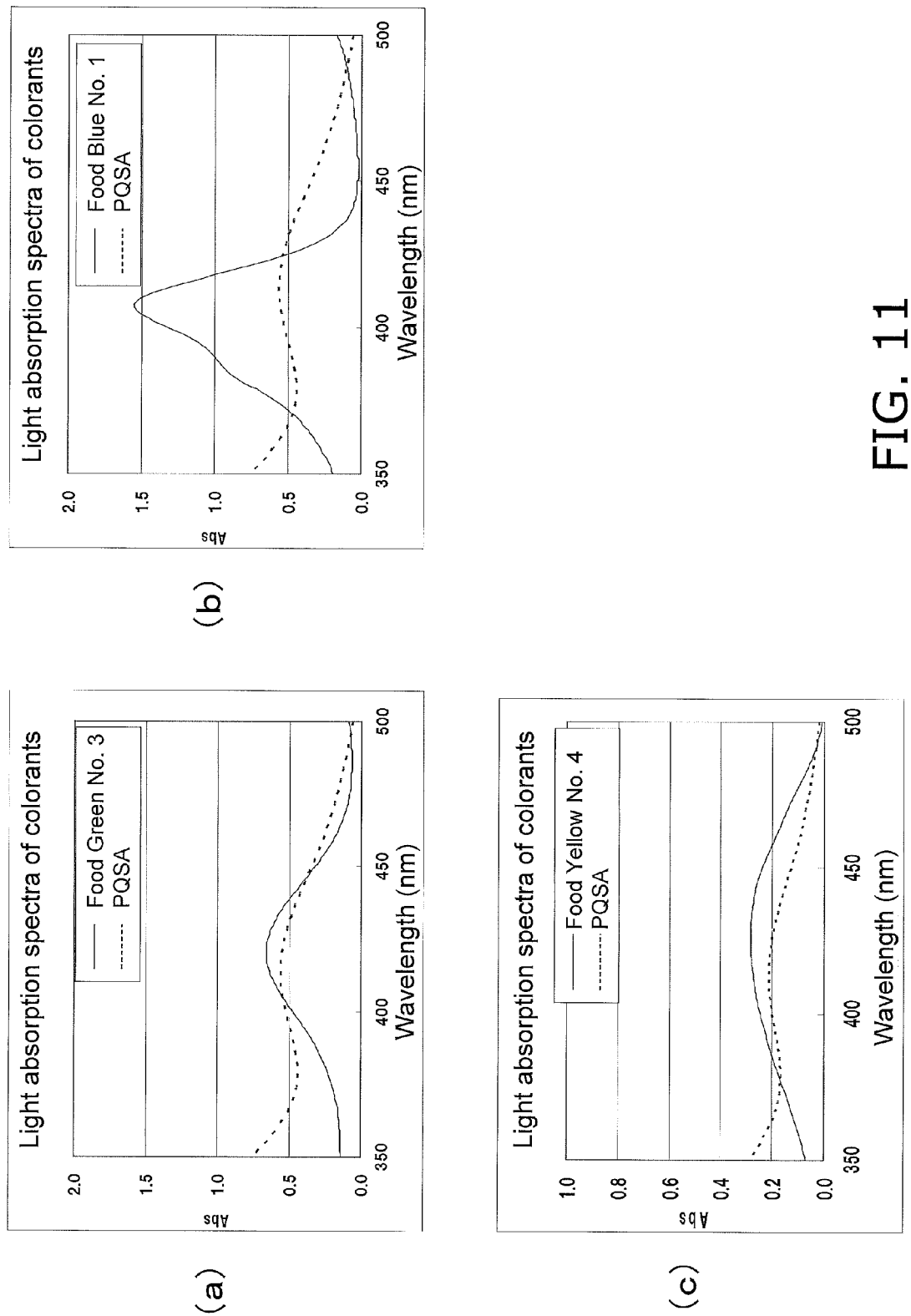
FIG. 11a is a graph of the absorption spectrum of Food Green No. 3 and PQSA.
FIG. 11b is a graph of the absorption spectrum of Food Blue No. 1 and PQSA.
FIG. 11c is a graph of the absorption spectrum of Food Yellow No. 4 and PQSA.

An example of a mediator with which the use of a light effect reducing agent (discussed below) can further reduce the effect that light exposure will have on measurement values is a mediator having an absorption band in the wavelength region of 400 to 500 nm. Examples include the PQSA (discussed below) shown in FIG. 11, the potassium ferricyanide shown in FIGS. 17a to 17c, ferrocenylmethyl dodecyl dimethyl ammonium bromide, and hexachlorooxamate.

There are no particular restrictions on the amount in which the mediator is added, but an example is 0.1 to 1000 mM, and preferably 1 to 500 mM, and more preferably 10 to 200 mM, per biosensor or per measurement.

Oxidoreductase

The oxidoreductase is, for example, glucose oxidase, lactate oxidase, cholesterol oxidase, bilirubin oxidase, glucose dehydrogenase, or lactate dehydrogenase. The amount of oxidoreductase is, for example, 0.01 to 100 U, and preferably 0.05 to 10 U, and more preferably 0.1 to 5 U, per measurement or per sensor. Among these, what is measured is preferably glucose, in which case the oxidoreductase is preferably glucose dehydrogenase or glucose oxidase.

As discussed above, the reagent component 9 includes an oxidoreductase such as glucose dehydrogenase, a mediator, a light effect reducing agent, and selectively includes a buffer, a polymer material, an enzyme stabilizer, a crystallization homogenizer, and the like as optional components, and to formulate the reagent component 9, these substances are dissolved in about 80% of the total water. The reagent solution in which these substances have been dissolved is dropped onto the blood component measurement counter electrode 6 (an example of a second electrode), the blood component measurement working electrode 5 (an example of a first electrode), and the blood component detection electrode 7 (an example of a third electrode) of the insulated substrate 4, and the solution is dried to form the reagent component 9.

During formulation, there is more water than anything else, then the mediator, then the light effect reducing agent, and then the other substances, but in a dried state, all of the water has been evaporated off, so there is more mediator than anything else, then the light effect reducing agent, and then the other substances.

Spacer 10

There are no particular restrictions on the material of the spacer 10, but it can be the same as the material of the insulated substrate 4, for example. Nor are there are any particular restrictions on the size of the spacer 10 (including the hot-melt or other adhesive layer), but an example is a total length of 5 to 100 mm, a width of 3 to 50 mm, and a thickness of 0.01 to 1 mm, and preferably a total length of 7 to 50 mm, a width of 3 to 20 mm, and a thickness of 0.05 to 0.5 mm, and more preferably a total length of 10 to 30 mm, a width of 3 to 10 mm, and a thickness of 0.05 to 0.25 mm. An I-shaped cutout that serves as the biological sample introduction path 12 for introducing blood is formed in the spacer 10.

Cover 11

Nor are there are any particular restrictions on the material of the cover 11, and the same material as for the insulated substrate 4 can be used, for example. The portion of the cover 11 corresponding to the ceiling of the biological sample introduction path 12 is preferably subjected to a hydrophilic treatment. The hydrophilic treatment can entail, for example, a method in which a surfactant is applied, or a method in which hydrophilic functional groups, such as hydroxyl groups, carbonyl groups, or carboxyl groups, are introduced on the surface of the cover 11 by plasma treatment or the like.

There are no particular restrictions on the size of the cover 11, but an example includes a total length of 5 to 100 mm, a width of 3 to 50 mm, and a thickness of 0.01 to 0.5 mm, preferably a total length of 10 to 50 mm, a width of 3 to 20 mm, and a thickness of 0.05 to 0.25 mm, and more preferably a total length of 15 to 30 mm, a width of 3 to 10 mm, and a thickness of 0.05 to 0.1 mm.

The air hole 14 is preferably formed in the cover 11, and the shape may be circular, elliptical, polygonal, or the like, and an example of the size is a maximum diameter of 0.01 to 10 mm, and preferably a maximum diameter of 0.05 to 5 mm, and more preferably a maximum diameter of 0.1 to 2 mm. This air hole 14 can be formed, for example, by piercing with a drill or a laser, or it may be formed during the molding of the cover 11 by using a mold that can form an air vent. Next, as shown in FIG. 3, the biosensor 2 can be manufactured by stacking the insulated substrate 4, the spacer 10, and the cover 11 in that order and then integrating them. This integration may be accomplished by sticking the three members together with an adhesive agent, or by thermally fusing them. Examples of adhesives that can be used include epoxy adhesives, acrylic adhesives, polyurethane adhesives, thermosetting adhesives (such as hot melt adhesives), and UV-setting adhesives.

The cover 11 is either transparent or semitransparent so that the flow of blood into the biological sample introduction path 12 can be viewed.

Measurement Device 30

As discussed above, the measurement device 30 has the main case 1, and the insertion slot 3 for the biosensor 2 is formed in the main case 1 (see FIG. 1). The input terminal component 8, which comes into contact with the biosensor 2, is provided at the back of the insertion slot 3.

As shown in FIG. 2, a voltage application component 15 for applying voltage, and a current-voltage converter 16 are connected via a switching circuit 17 to the input terminal component 8.

More specifically, an applied voltage part 18 of the voltage application component 15 is connected to the switching circuit 17, the input terminal component 8, the blood component measurement working electrode 5, the reagent component 9, the blood component measurement counter electrode 6, and the blood component detection electrode 7 of the biosensor 2, and to a reference voltage part 19 of the voltage application component 15.

If we let the voltage of the applied voltage part 18 be 300 mV and the voltage of the reference voltage part 19 be 200 mV, for example, a voltage of 100 mV is applied between the blood component measurement working electrode 5 and the blood component measurement counter electrode 6.

In this embodiment, the voltage of the reference voltage part 19 is held constant while the voltage of the applied voltage part 18 is varied to obtain a voltage waveform.

The reason for providing the reference voltage part 19 is to reduce the effect of noise on the supply voltage from a power supply 20.

At any rate, when current based on the voltage difference between the blood component measurement working electrode 5 and the blood component measurement counter electrode 6 flows between the blood component measurement working electrode 5 and the blood component measurement counter electrode 6, and that current is converted into voltage, that is expressed in FIG. 2 as a current-voltage converter (such as a resistor provided between the blood component measurement counter electrode 6 and the reference voltage part 19).

That is, voltage is applied through a controller 21 to the voltage application component 15, at which point the current flowing to the biosensor 2 is converted by the current-voltage converter 16 into voltage. After this, the voltage is digitized by an A/D converter 22, and this digitized voltage is compared to a threshold by a determination means 23.

Glucose values sensed by the biosensor 2, and determination results produced by the determination means 23 are displayed on a display component 24 connected to the controller 21.

The power supply 20 in FIG. 2 is used to supply power to the various components. 25 is a memory that has a calibration table and a calibration curve produced ahead of time from environment temperatures or a table composed of applied voltages, application times, and so forth during glucose measurement, or hematocrit values.

The controller 21 is connected to a clock 26, and the controller 21 is configured to execute various kinds of control operation by using the indicated time or the elapsed time of the clock 26.

A correction means 27 is provided inside the controller 21, and the measurement accuracy of measured blood glucose levels is increased by correcting them while taking into account the effect of various kinds of harmful substances or the hematocrit values.

Use of Biological Sample Measurement System 100

When the biosensor 2 is inserted into the insertion slot 3, the input terminal component 8 is connected to the blood component measurement working electrode 5, the blood component measurement counter electrode 6, and the blood component detection electrode 7. The switch (not shown) of the insertion slot 3 is depressed by the biosensor 2. When the controller 21 concludes from the depression of the switch that the biosensor 2 has been mounted, the measurement device 30 goes into a state of waiting for a sample. This sample waiting state is a state in which the applied voltage part 18 has started the application of voltage between the blood component measurement working electrode 5 and the blood component detection electrode 7 via the input terminal component 8 under the control of the controller 21, after the current-voltage converter 16 has started current measurement, but before a liquid sample has been supplied for measurement.

When the user deposits a liquid sample in the blood supply opening 13 of the biosensor 2, the liquid sample is drawn by capillary action from the blood supply opening 13 into the biological sample introduction path 12.

Examples of liquid samples that can be used include blood, perspiration, urine, and other such liquid samples with a biological origin, liquid samples that come from the environment, and liquid samples that come from food. For instance, if the biosensor 2 is used as a blood glucose level sensor, the user prick's his own finger, palm, arm, or the like, squeezes out a small amount of blood, and provides this blood as a liquid sample for measurement in the biosensor 2.

When the liquid sample reaches the blood component measurement working electrode 5 and the blood component detection electrode 7, there is a change in the current value received by controller 21 via the current-voltage converter 16. The controller 21 concludes from this change that the liquid sample has been drawn into the biosensor 2. Measurement is started once this drawing in of the liquid sample has been detected.

Within the biosensor 2, the enzyme, mediator, and other such components of the reagent component 9 are dissolved in the liquid sample. In this way, the liquid sample, the enzyme, and the mediator are brought into contact with each other on the blood component measurement working electrode 5 and the blood component measurement counter electrode 6 of the biosensor 2.

Under control of the controller 21, the switching circuit 17 connects to the reference voltage part 19 and the current-voltage converter 16. This applies voltage between the blood component measurement working electrode 5 and the blood component measurement counter electrode 6. The voltage that is applied here will be described in detail below through reference to FIGS. 4a and 4b, but the current produced between the blood component measurement working electrode 5 and the blood component measurement counter electrode 6 is transmitted to the current-voltage converter 16 in a second application period (discussed below).

The current that flows to the current-voltage converter 16 is converted into voltage. This voltage is then converted into pulses by the A/D converter 22. The controller 21 calculates the concentration of a specific component by making corrections with the correction means 27 from these pulses. The value calculated by the controller 21 is displayed on the display component 24. Other information for the user may also be displayed here.

When the measurement is finished, the user can remove the biosensor 2 from the insertion slot 3.

Applied Voltage During Measurement

Figure 4:
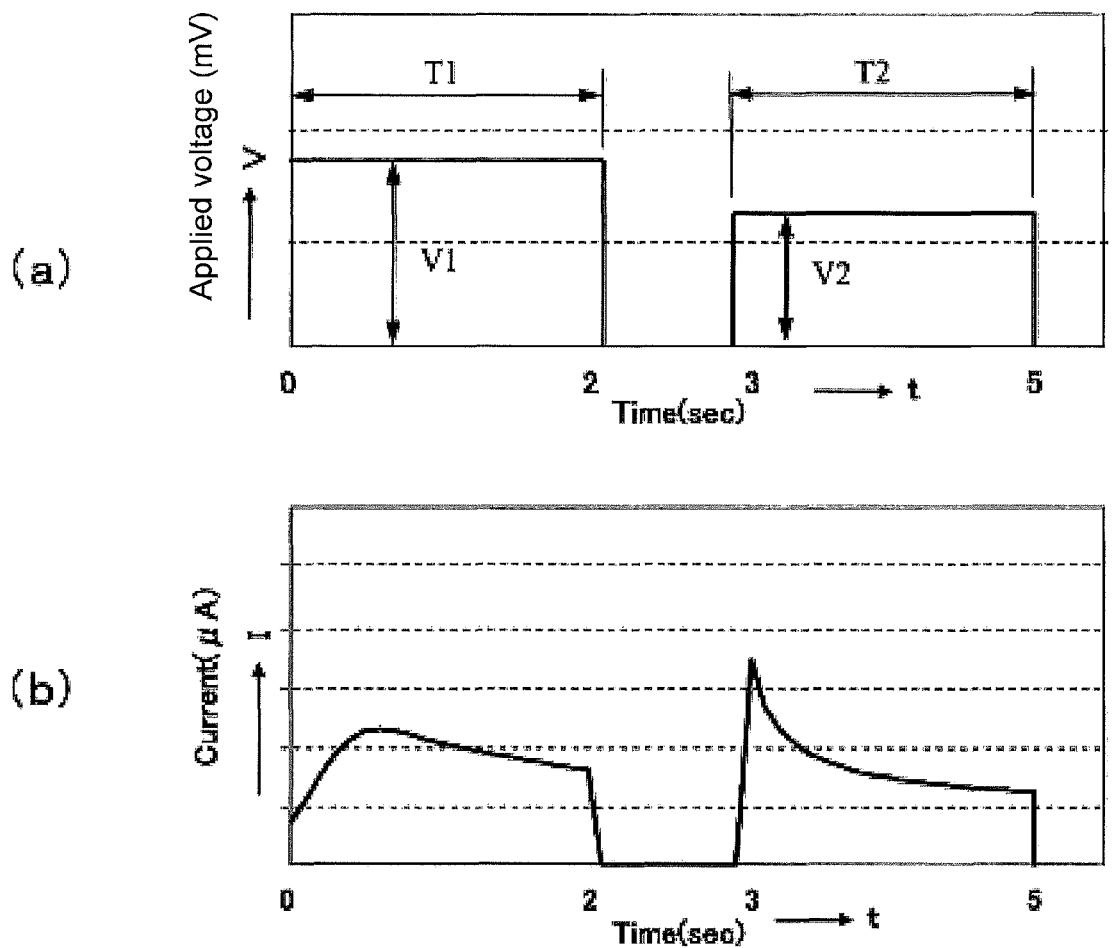
FIG. 4a is a graph of the operating state of a measurement device in the biological sample measurement system in FIG. 1.
FIG. 4b is a graph of the operating state of a measurement device in the biological sample measurement system in FIG. 1 in a measurement device.

Next, the applied voltage during measurement will be described through reference to FIGS. 4a and 4b. FIG. 4a is a graph of the applied voltage, and FIG. 4b is a graph of the signal produced by the application of voltage.

In the application shown in FIG. 4a, there are two application patterns, namely, a first application period and a second application period, which flank a down time (of one second, for example).

The first application period is also called a preprocessing voltage application mode or a pre-application mode. This first application period is the period in which the applied voltage V1 (such as 0.35 V) shown in FIG. 4a is applied as a preprocessing voltage for an application time T1 (such as 2 seconds), between the blood component measurement working electrode 5 and the blood component measurement counter electrode 6, via the input terminal component 8, under a command from the controller 21.

The down time (down mode) is the period in which the preprocessing voltage that was being applied between the blood component measurement working electrode 5 and the blood component measurement counter electrode 6 via the input terminal component 8 after the preprocessing voltage application period (first application period) is stopped. That is, the oxidoreductase and the glucose in the blood are allowed to react for a specific length of time.

The second application period is a measured voltage application mode, and is the period in which the applied voltage V2 (such as 0.25 V) shown in FIG. 4a is applied for an application time T2 (such as for 2 seconds, 3 seconds after the start of measurement) between the blood component measurement working electrode 5 and the blood component measurement counter electrode 6 via the input terminal component 8 after the down time, and biological information such as a blood glucose level is measured.

As discussed above, when the voltage application pattern shown in FIG. 4a is applied for the first application period, the down time, and the second application period, the electron carrier (mediator) in a reduced state produced on the blood component measurement working electrode 5 and the blood component measurement counter electrode 6 is oxidized by enzyme reaction, and this oxidation current is detected. The oxidation current detected by the biological sample measurement system 100 is outputted as a signal waveform as shown in FIG. 4b.

The target biological information (such as a blood glucose level (glucose concentration)) is measured from this signal from the biosensor 2 (the waveform on the right side in FIG. 4b).

In FIG. 4a, a down time in which no voltage is applied between is provided the application times T1 and T2, but the present invention is not limited to this.

Also, in FIGS. 4a and 4b, the applied voltage V1 is higher than the applied voltage V2, but this is not the only option, and the applied voltage V2 may instead be higher than the applied voltage V1, or the applied voltage V1 and the applied voltage V2 may be the same.

Reagent Component 9 and Light Effect Reducing Agent Contained Therein

Figure 5:
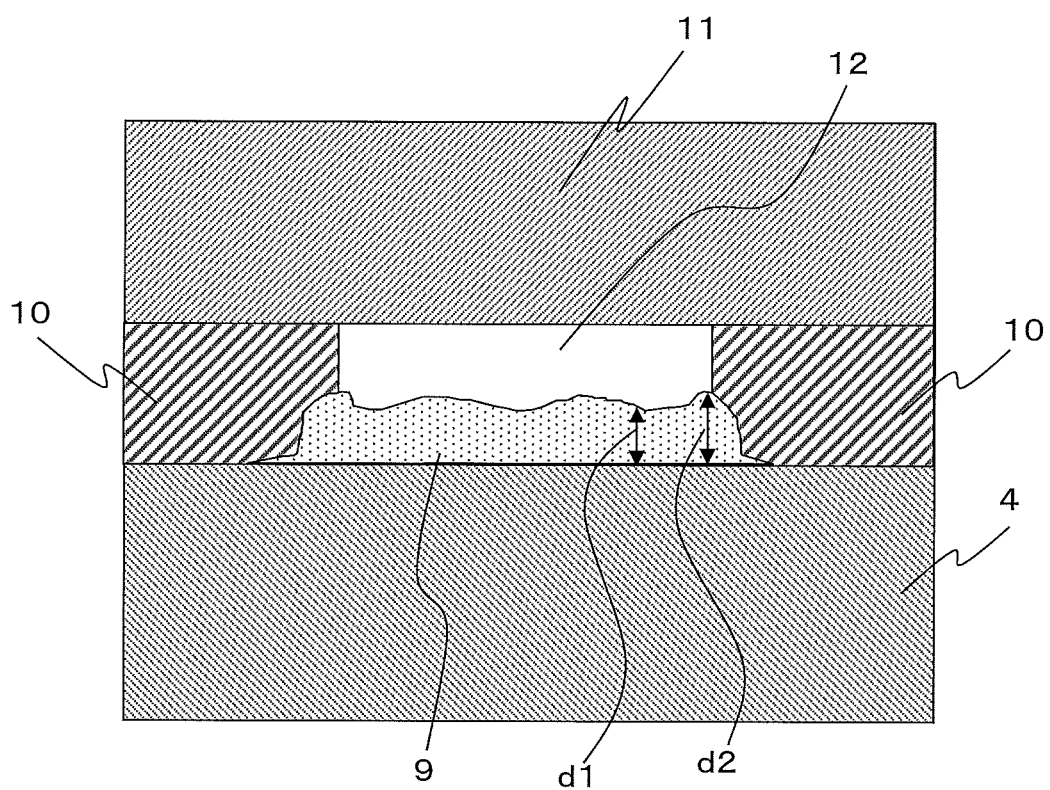
FIG. 5 is a cross section of the reagent component of the biosensor in FIG. 1.

In the above configuration, the most salient feature of this embodiment is that a light effect reducing agent was admixed into the reagent component 9. As can be understood from FIG. 3, the reagent component 9 is circular in plan view, and when it is cut in the middle portion, the resulting state is as shown in FIG. 5. Specifically, the reagent component 9 is formed in a substantially columnar shape.

That is, in a plan view state on the insulated substrate 4 as shown in FIG. 3, the reagent component 9 is such that the thickness d2 of the outer peripheral portion is greater than the thickness d1 of the inner peripheral portion.

Thus making the thickness d2 of the outer peripheral portion greater than the thickness d1 of the inner peripheral portion of the reagent component 9 in a plan view state on the insulated substrate 4 can be easily accomplished during the manufacture of the reagent component 9.

Specifically, as discussed above, the reagent component 9 is formed by adding glucose dehydrogenase or another such oxidoreductase, a mediator, and a light effect reducing agent to water (approximately 80% of the total), selectively adding a buffer, a polymeric material, an enzyme stabilizer, a crystal homogenizer, and the like as optional components, dropping the resulting reagent solution onto the insulated substrate 4, and then drying this solution.

In a state in which the reagent solution has been dropped, the drying here is performed from the outer peripheral portion, so overall drying is performed while moving toward the outer periphery, and this results in what is known as a "coffee ring" state. That is, in a dried state the reagent component 9 is such that the thickness d2 of the outer peripheral portion is greater than the thickness d1 of the inner peripheral portion in a plan view state on the insulated substrate 4.

In this dried state, the light effect reducing agent is distributed more to the surface portion (the cover 11 side) than in the interior of the reagent component 9. The reason for this is believed to be that the chemical structure formula of the light effect reducing agent being used has an effect, although there are some details that are still not fully understood. The light effect reducing agent can be Food Blue No. 1 (Brilliant Blue FCF), Food Green No. 3 (Fast Green FCF), Food Yellow No. 4 (tartrazine), or the like.

Figure 6:
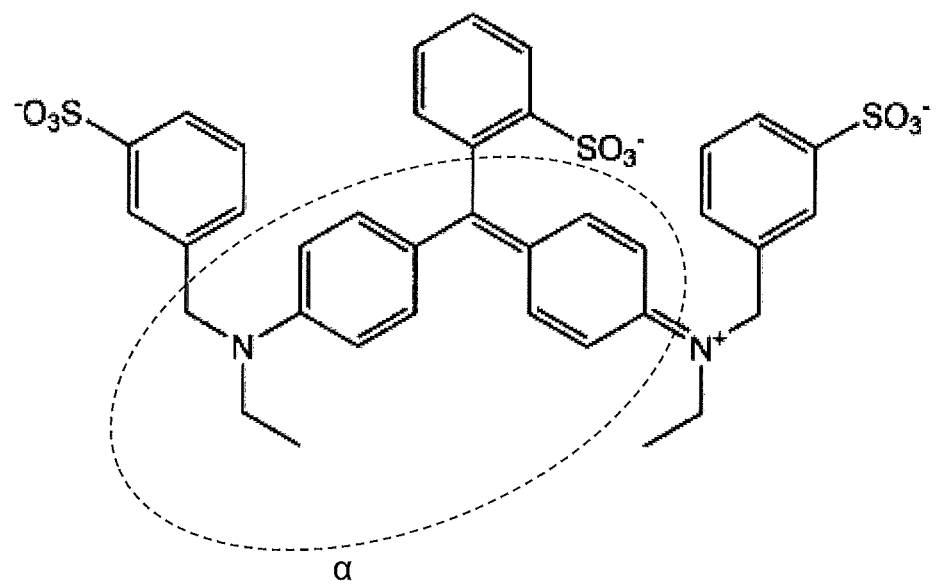
FIG. 6 shows the chemical structure formula for Food Blue No. 1 (Brilliant Blue FCF), which is an example of the light effect reducing agent contained in the reagent component of the biosensor in FIG. 1.
Figure 7:
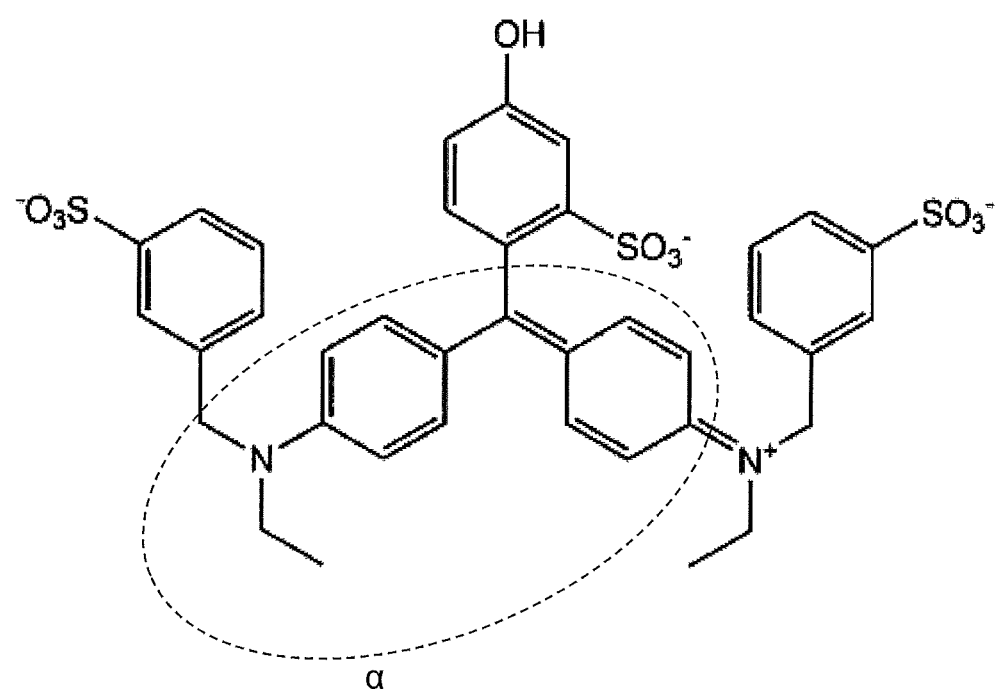
FIG. 7 shows the chemical structure formula for Food Green No. 3 (Food Fast Green FCF), which is an example of the light effect reducing agent contained in the reagent component of the biosensor in FIG. 1.
Figure 8:
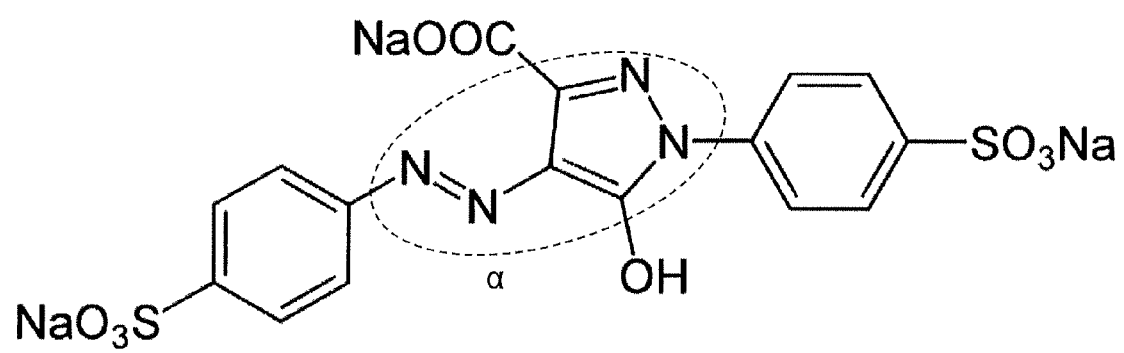
FIG. 8 shows the chemical structure formula for Food Yellow No. 4 (tartrazine), which is an example of the light effect reducing agent contained in the reagent component of the biosensor in FIG. 1.

FIG. 6 shows the chemical structure formula for Food Blue No. 1 (Brilliant Blue FCF), FIG. 7 shows the chemical structure formula for Food Green No. 3 (Fast Green FCF), and FIG. 8 shows the chemical structure formula for Food Yellow No. 4 (tartrazine), as light effect reducing agents. These chemical structure formulas for Food Blue No. 1, Food Green No. 3, and Food Yellow No. 4 all have a hydrophobic benzene ring portion and a hydrophilic benzene ring portion. The "benzene ring portion" encompasses benzene substitute, benzene reductant, benzene derivative, and so forth, and may have two or more substituents.

With the Food Blue No. 1 shown in FIG. 6, the hydrophilic benzene ring portion indicates a sulfophenyl portion of the chemical structure formula, and the hydrophobic benzene ring portion indicates a 4-ethylaminophenyl-methylidenylcyclohexadiene portion (the $\alpha$ portion surrounded by the dotted line) of the chemical structure formula. With the Food Green No. 3 shown in FIG. 7, the hydrophilic benzene ring portion indicates a sulfophenyl or 4-hydroxy-2-sulfophenyl portion of the chemical structure formula, and the hydrophobic benzene ring portion indicates a 4-ethylaminophenyl-methylidenylcyclohexadiene portion (the $\alpha$ portion surrounded by the dotted line) of the chemical structure formula. With the Food Yellow No. 4 shown in FIG. 8, the hydrophilic benzene ring portion indicates a sulfophenyl portion of the chemical structure formula, and the hydrophobic benzene ring portion indicates a 4-hydrazonopyrazole portion (the α portion surrounded by the dotted line) of the chemical structure formula.

Figure 9:
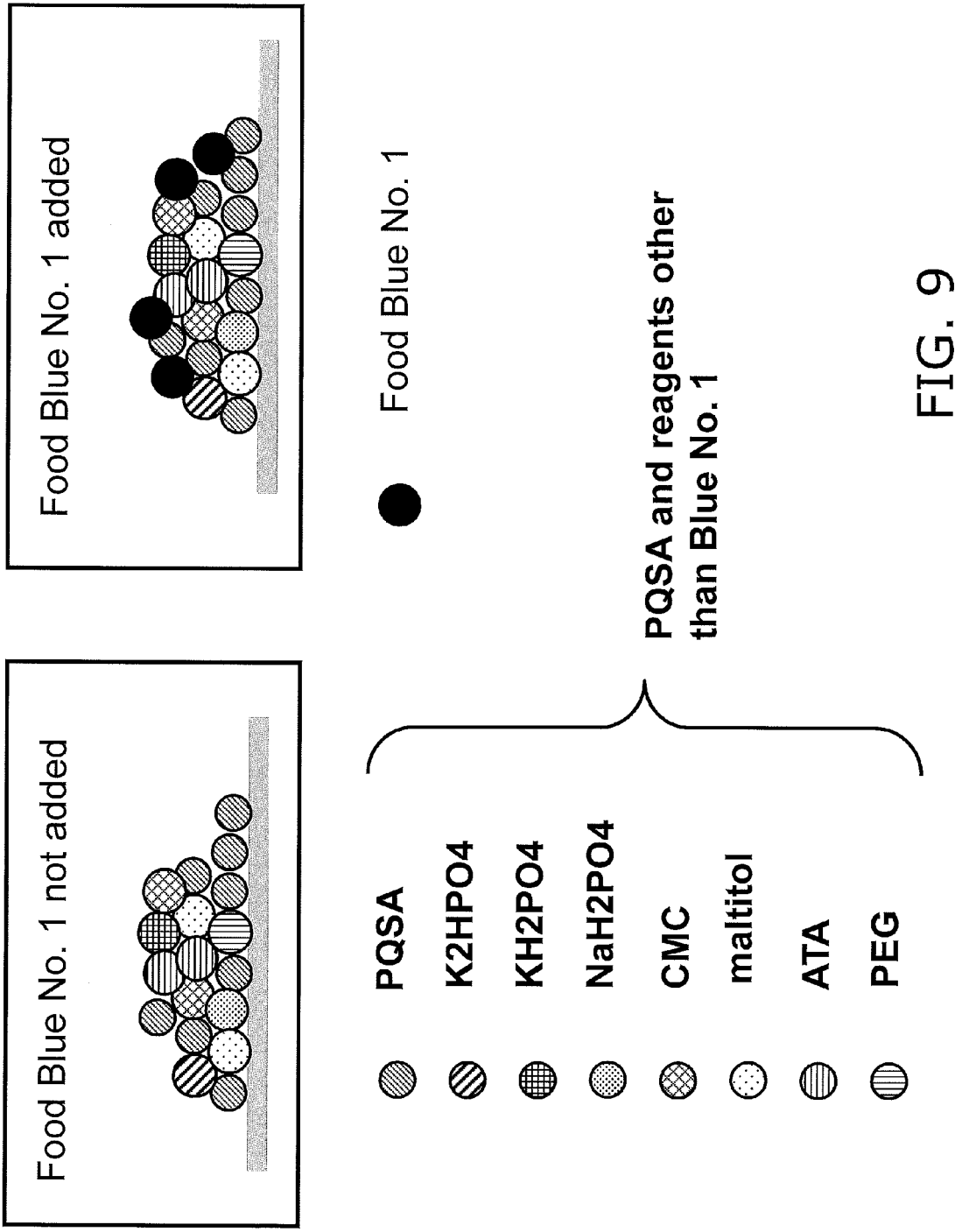
FIG. 9 is a simplified diagram of the state of the reagent component when Food Blue No. 1 has and has not been added.

Accordingly, during drying, in a situation in which drying occurs while the above-mentioned inward portion moves toward the outer periphery, the drying proceeds in a state in which the hydrophobic benzene ring portion appears on the surface side (the cover 11 side), that is, in a situation in which it comes up on the surface side of the reagent component 9, and as a result, the light effect reducing agent is distributed more in the surface portion (on the cover 11 side) than in the interior of the reagent component 9. FIG. 9 is a simplified diagram of the reagent in a state in which Food Blue No. 1 has not been added, and the reagent in a state in which Food Blue No. 1 has been added. As shown in FIG. 9, with the reagent component 9 in which Food Blue No. 1 has been added, the Food Blue No. 1 (an example of a light effect reducing agent) is distributed more at the surface of the reagent component 9.

This state also appears as a state in which the hydrophobic benzene ring portion of the light effect reducing agent is disposed toward the surface layer side of the reagent component 9.

This is extremely important, and as discussed above, even though the light effect reducing agent is admixed in only a small amount more than the mediator, it will be more prevalent in the surface portion of the reagent component 9 than in the interior, which effectively reduces the effect of light on the reagent component 9.

To continue the description into this point, the reagent component 9 is affected by light, and its mediator function in particular is degraded, so suppressing this is the most salient feature in this embodiment.

The mediator of the reagent component 9 used in this embodiment is affected by light of 400 to 500 nm, for example, so the light effect reducing agents that is used here is Food Blue No. 1 (Brilliant Blue FCF), Food Green No. 3 (Fast Green FCF), or Food Yellow No. 4 (tartrazine), as mentioned above.

Food Blue No. 1 (Brilliant Blue FCF), Food Green No. 3 (Fast Green FCF), and Food Yellow No. 4 (tartrazine) absorb light of 400 to 500 nm, and are themselves degraded (for example, this is also expressed as a state in which the color fades), but this light of 400 to 500 nm is correspondingly less likely to reach the mediator, and as a result the function of the mediator is less likely to be degraded.

Accordingly, in the measurement of a biological sample using the biosensor 2 of this embodiment, such as in the measurement of a blood glucose level, the electron transfer function of the mediator is appropriately exhibited, and as a result, the proper measurement of the biological sample can be carried out.

Food Green No. 3, Food Blue No. 1, and Food Yellow No. 4, which are the light effect reducing agents used in this embodiment, will now be described in further detail.

FIG. 10 is a table of the maximum absorption wavelengths (nm) of Food Blue No. 1, Food Green No. 3, and Food Yellow No. 4, the absorbancy (Abs) of these wavelengths, the concentration (c(M)) at which this absorbancy is exhibited, the molar extinction coefficient ($\epsilon$), and the ratio of the molar extinction coefficient to PQSA, which is an example of a mediator, along with the PQSA. Abs=$\epsilon$cl (l is the cell length, and is set to 1 cm).

FIG. 11a is a graph of the absorption spectrum of Food Green No. 3 and PQSA near 350 to 500 nm. FIG. 11b is a graph of the absorption spectrum of Food Blue No. 1 and PQSA near 350 to 500 nm. FIG. 11c is a graph of the absorption spectrum of Food Yellow No. 4 and PQSA near 350 to 500 nm. In FIG. 11a, the concentration of Food Green No. 3 is 0.5 mM, and the concentration of PQSA is 0.1 mM. In FIG. 11b, the concentration of Food Blue No. 1 is 0.1 mM, and the concentration of PQSA is 0.1 mM. In FIG. 11c, the concentration of Food Yellow No. 4 is 0.01 mM, and the concentration of PQSA is 0.1 mM.

As shown in FIGS. 11a, 11b, and 11c, Food Green No. 3, Food Blue No. 1, and Food Yellow No. 4 have absorption near the wavelength (414 nm) at which PQSA is affected. As shown in FIG. 10, Food Green No. 3, Food Blue No. 1, and Food Yellow No. 4 have an $\epsilon$ ratio higher than 1 near this wavelength (414 nm), so they tend to absorb light more than PQSA does, and degradation of PQSA caused by light absorption can be prevented.

Method for Manufacturing Biosensor

Figure 12:
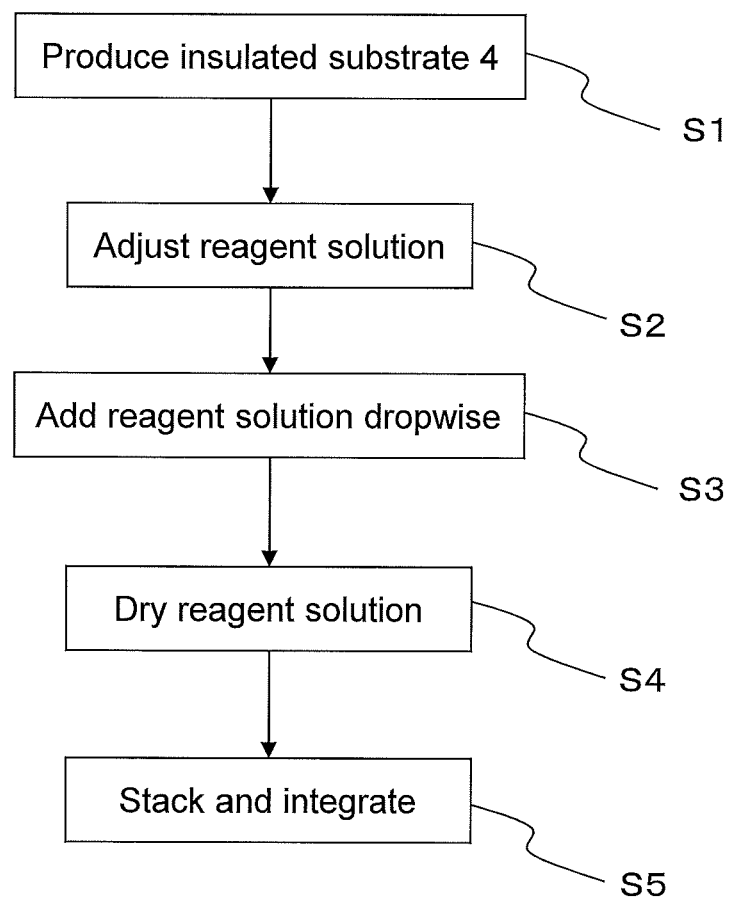
FIG. 12 is a flowchart of a method for manufacturing the biosensor in this embodiment.

A method for manufacturing a biosensor will now be described. FIG. 12 is a flowchart of a method for manufacturing a biosensor.

As shown in S1 of FIG. 12, first the insulated substrate 4 is produced, on which the blood component measurement working electrode 5, the blood component measurement counter electrode 6, and the blood component detection electrode 7 have been formed.

Next, as shown in S2 of FIG. 12, a reagent solution is prepared. This reagent solution is produced by dissolving in water at least an oxidoreductase that will subject the substance to be measured to dehydrogenation or oxidation, a mediator that exchanges electrons with the oxidoreductase, and a light effect reducing agent, and selectively dissolving a buffer, a polymeric material, an enzyme stabilizer, a crystal homogenizer, or the like as optional components.

Next, as shown in S3 of FIG. 12, the reagent solution is dropped onto the insulated substrate 4 on which the various electrodes have been formed, so that the solution will reach the blood component measurement working electrode 5, the blood component measurement counter electrode 6, and the blood component detection electrode 7 (an example of a placement step).

Next, as shown in S4 of FIG. 12, the reagent solution placed on the insulated substrate 4 is dried (an example of a drying step).

Finally, as shown in S5 of FIG. 12, the insulated substrate 4, the spacer 10, and the cover 11 are stacked in that order and integrated to manufacture a biosensor.

Working Example

The above embodiment will be described in further detail by giving a working example.

Sunlight Exposure Effect of Food Green No. 3

FIG. 13a is a graph of the effect of sunlight exposure when Food Green No. 3 is used. FIG. 13b is a graph of the effect of sunlight exposure when Food Blue No. 1 is used. FIG. 13c is a graph of the effect of sunlight exposure when Food Yellow No. 4 is used.

In FIG. 13a, for example, a reagent component was produced by adding a reagent from the table shown in FIG. 14a to water to produce a reagent solution, and then drying this reagent solution.

The composition of the reagent solution was 91.25 wt % (weight %) water, 7.41% glucose dehydrogenase (the enzyme), 0.08% Food Green No. 3 is (molecular weight of 808.87), a total of 0.2% $K_2HPO_4$, $KH_2PO_4$, and $NaH_2PO_4$ (a buffer), 0.13% CMC (carboxymethyl cellulose; a polymer material, used as an adhesive), 0.04% ATA (3-amino-1,2,4-triazole; an enzyme stabilizer), 0.17% maltitol (a storage stabilizer), 0.70% PQSA (a mediator), and 0.03% other selected components. This produced a reagent solution with a concentration of 1.0 mM of Food Green No. 3.

Also, a reagent solution with a concentration of 10 mM of Food Green No. 3 was produced from the composition shown in FIG. 14b. The concentration of PQSA (molecular weight of 309.28) was 22.6 mM in each case.

Meanwhile, a reagent solution to which no colorant was added was also produced as a comparative example. These three different reagent solutions were used to produce reagent components, and the effect on measurement values by exposure to sunlight was checked.

Reagent components were produced using this colorant-free reagent solution, the reagent solution containing 1 mM of Food Green No. 3, and the reagent solution containing 10 mM of Food Green No. 3, and these reagent components were used to compare the measurement results when sample solutions were and were not exposed to sunlight for one hour. FIGS. 14a and 14b show the weight percentage (wt %) of the various components of the reagent component after drying.

More specifically, the average value of five measurements of a sample solution (a 42% Hct solution having a glucose concentration of about 48 mg/dL) when using a reagent containing no colorant and not exposed to sunlight was 41.5 mg/dL, and the average value of five measurements a sample solution (a 42% Hct solution having a glucose concentration of about 48 mg/dL) when using a reagent containing no colorant after exposure to sunlight was 87.2 mg/dL. Therefore, the deviation in measurement value when using the reagent without a colorant, from when there was no light exposure, was (87.2−41.5)/41.5=1.101, or 110.1%.

Specifically, the deviation rate in the graph of FIG. 13 is found from the formula: (the measured value after sunlight exposure−the measured value without sunlight exposure) ÷the measured value without sunlight exposure.

The average value of five measurements of the above-mentioned sample solution when using a reagent containing 1 mM of Food Green No. 3 and not exposed to sunlight was 41.7 mg/dL, and the average value of five measurements this sample solution when using a reagent containing 1 mM of Food Green No. 3 with exposure to sunlight was 76.4 mg/dL. Therefore, the deviation in measurement value when using the reagent containing 1 mM of Food Green No. 3, from when there was no light exposure, was (76.4−41.7)/41.7=0.833, or 83.3%.

The average value of five measurements of the above-mentioned sample solution when using a reagent containing 10 mM of Food Green No. 3 and not exposed to sunlight was 40.9 mg/dL, and the average value of five measurements this sample solution when using a reagent containing 10 mM of Food Green No. 3 with exposure to sunlight was 62.5 mg/dL. Therefore, the deviation in measurement value when using the reagent containing 10 mM of Food Green No. 3, from when there was no light exposure, was (62.5−40.9)/40.9=0.526, or 52.6%.

These results are given in FIG. 13a. It can be seen that the case of 1 mM, as compared with the case of no colorant, the deviation from no sunlight exposure is smaller, and sunlight exposure has less of an effect. When comparing the use of 10 mM to the use of 1 mM, it can be seen that the suppression effect is better when the amount of the colorant is increased.

As discussed above, a reduction in the effect of sunlight exposure was exhibited when the concentration of Food Green No. 3 in the reagent solution for forming the reagent component 9 was at least 1 mM, but since a reduction was obtained when using a reagent solution in which the concentration of Food Green No. 3 was 10 mM (FIG. 13a), the concentration of Food Green No. 3 in the reagent solution for forming the reagent component 9 is more preferably within the range of at least 1 mM and no more than 10 mM. Also, the molar ratio of the Food Green No. 3 here to the mediator after drying is at least 0.0442 (=1/22.6) and no more than 0.442 (=10/22.6). That is, Food Green No. 3 reduces the sunlight exposure effect at a molar ratio of at least 0.0442 to the mediator, and this molar ratio is more preferably 0.442 or less.

As shown in FIG. 14, the sunlight exposure effect is reduced when the weight ratio of Food Green No. 3 to the entire reagent component after drying is at least 6.01%, and this weight ratio is preferably no more than 39.02%.

Sunlight Exposure Effect of Food Blue No. 1

In FIG. 13b, for example, a measurement reagent was produced by adding a reagent from the table shown in FIG. 15a to water to produce a reagent solution, and then drying this reagent solution.

The composition of the reagent solution was 91.25 wt % water, 7.41 wt % glucose dehydrogenase (the enzyme), 0.08% Food Blue No. 1 (molecular weight of 792.86), a total of 0.2% $K_2HPO_4$, $KH_2PO_4$, and $NaH_2PO_4$ (a buffer), 0.13% CMC (carboxymethyl cellulose; a polymer material, used as an adhesive), 0.04% ATA (3-amino-1,2,4-triazole; an enzyme stabilizer), 0.17% maltitol (a storage stabilizer), 0.70% PQSA (a mediator), and 0.03% other selected components. This produced a reagent solution with a concentration of 1 mM of Food Blue No. 1.

Also, a reagent solution with a concentration of Food Blue No. 1 of 5 mM was produced in the composition shown in FIG. 15b. The molar concentration of PQSA (molecular weight of 309.28) was 22.6 mM in each case.

Reagent components were produced using the reagent solution containing 1 mM of Food Blue No. 1 and the reagent solution containing 5 mM of Food Blue No. 1, and these reagent components were used to compare the measurement results when sample solutions (the same as with Food Green No. 3) were and were not exposed to sunlight for one hour. FIGS. 15a and 15b show the weight percentage (wt %) of the various components of the reagent component after drying.

The deviation rate when using the various reagent components was then found by the same calculation as that used for Food Green No. 3, which revealed the deviation rate to be 84.3% with 1 mM of Food Blue No. 1, and 24.7% with 5 mM of Food Blue No. 1.

These results are shown in FIG. 13b along with the results obtained with a reagent to which no colorant was added (comparative example). As shown in FIG. 13b, it can be seen that the addition of Food Blue No. 1 reduces the effect of sunlight exposure. Also, a comparison between 1 mM and 5 mM reveals that this reduction is enhanced by increasing the added amount of colorant.

As described above, the effect of sunlight exposure is reduced when the concentration of Food Blue No. 1 in the reagent solution for forming the reagent component 9 is at least 1 mM. Also, it can be seen from FIG. 13b that a reduction in this effect is obtained when using a reagent solution in which the concentration of Food Blue No. 1 is 5 mM, so it is more preferable for the concentration of Food Blue No. 1 in the reagent solution used to form the reagent component 9 to be within a range of at least 1 mM and no more than 5 mM. Also, the molar ratio of the Food Blue No.

1 here to the mediator after drying is at least 0.0442 (=1/22.6) and no more than 0.221 (=5/22.6). That is, Food Blue No. 1 exhibits a reduction in the effect of sunlight exposure at a molar ratio of at least 0.0442 to the mediator, and this molar ratio is more preferably 0.221 or less.

Further, as shown in FIG. 15, the effect of sunlight exposure will be reduced if the weight ratio of the Food Blue No. 1 to the entire reagent component after drying is at least 5.90%, and it is more preferable for this weight ratio to be no more than 23.87%.

Sunlight Exposure Effect of Food Yellow No. 4

In FIG. 13c, for example, a measurement reagent was produced by adding a reagent from the table shown in FIG. 16a to water to produce a solution, and then drying this solution.

The composition of the reagent solution was 91.25 wt % water, 7.41 wt % glucose dehydrogenase (the enzyme), 0.01% Food Yellow No. 4 (molecular weight of 534.37), a total of 0.2% $K_2HPO_4$, $KH_2PO_4$, and $NaH_2PO_4$ (a buffer), 0.13% CMC (carboxymethyl cellulose; a polymer material, used as an adhesive), 0.04% ATA (3-amino-1,2,4-triazole; an enzyme stabilizer), 0.17% maltitol (a storage stabilizer), 0.70% PQSA (a mediator), and 0.03% other selected components. This produced a reagent solution with a concentration of 1 mM of Food Yellow No. 4.

Also, a solution with a concentration of Food Yellow No. 4 of 5 mM was produced in the composition shown in FIG. 16b. Further, a solution with a concentration of Food Yellow No. 4 of 10 mM was produced in the composition shown in FIG. 16c. Meanwhile, a reagent to which no colorant was added was also produced for the sake of comparison. The molar concentration of PQSA (molecular weight of 309.28) was 22.6 mM in each case.

Reagent components were produced using the reagent solution containing 1 mM of Food Yellow No. 4, the reagent solution containing 5 mM of Food Yellow No. 4, and the reagent solution containing 10 mM of Food Yellow No. 4, and these reagent components were used to compare the measurement results when sample solutions (the same as with Food Green No. 3) were and were not exposed to sunlight for one hour. FIGS. 16a to 16c show the weight percentage (wt %) of the various components of the reagent component after drying.

The deviation rate when using the various reagent components was then found by the same calculation as that used for Food Green No. 3, which revealed the deviation rate to be 66.3% with 1 mM of Food Yellow No. 4 , 28.4% with 5 mM of Food Yellow No. 4, and 19.5% with 10 mM of Food Yellow No. 4.

These results are shown in FIG. 13c along with the results obtained with a reagent to which no colorant was added (comparative example). As shown in FIG. 13c, the addition of Food Yellow No. 4 lowers the deviation from when there is no sunlight exposure, as compared to when there is no colorant, it can be seen that the effect of sunlight exposure is reduced. Also, a comparison between 1 mM, and 5 mM, and 10 mM reveals that this reduction is enhanced by increasing the added amount of colorant.

As described above, the effect of sunlight exposure is reduced when the concentration of Food Yellow No. 4 in the reagent solution for forming the reagent component 9 is at least 1 mM. Also, it can be seen from FIG. 13c that a reduction in this effect is obtained when using a reagent solution in which the concentration of Food Yellow No. 4 is 10 mM, so it is more preferable for the concentration of Food Yellow No. 4 in the reagent solution used to form the reagent component 9 to be within a range of at least 1 mM and no more than 10 mM. Also, the molar ratio of the Food Yellow No. 4 here to the mediator after drying is at least 0.0442 (=1/22.6) and no more than 0.442 (=10/22.6). That is, Food Yellow No. 4 exhibits a reduction in the effect of sunlight exposure at a molar ratio of at least 0.0442 to the mediator, and this molar ratio is more preferably 0.442 or less.

Further, as shown in FIG. 16, the effect of sunlight exposure will be reduced if the weight ratio of the Food Yellow No. 4 to the entire reagent component after drying is at least 4.06%, and it is more preferable for this weight ratio to be no more than 29.71%.

What is particularly noteworthy in this embodiment is that the biosensors 2 themselves can reduce degradation by light. Conventional products were sometimes affected by light to the extent that they were no longer practically usable, but even when the biosensor 2 is taken out of its holding vessel and left out for an hour, it will be affected by light less than a conventional product (with no light effect reducing agent), and will still be usable in practical applications.

Features, etc.

(1)

The biosensor 2 in the above embodiment comprises the blood component measurement working electrode 5, the blood component measurement counter electrode 6, and the reagent component 9. The reagent component 9 is provided near the blood component measurement working electrode 5 and the blood component measurement counter electrode 6. The reagent component 9 includes a mediator, an oxidoreductase, and a substance that absorbs light with a wavelength of 400 to 500 nm.

This reduces degradation through absorption by the mediator of light with a wavelength of 400 to 500 nm.

(2)

The biosensor 2 in the above embodiment comprises the blood component measurement working electrode 5, the blood component measurement counter electrode 6, and the reagent component 9. The reagent component 9 is provided near the blood component measurement working electrode 5 and the blood component measurement counter electrode 6. The reagent component 9 includes a mediator, an oxidoreductase, and a light effect reducing agent.

The light effect reducing agent reduces degradation of the mediator due to the effect of light. This reduces degradation when the mediator is exposed to sunlight or the like.

(3)

The biosensor 2 in the above embodiment comprises the insulated substrate 4 (an example of a substrate) on the surface of which are disposed the blood component measurement working electrode 5 and/or the blood component measurement counter electrode 6. The reagent component 9 is disposed on one or both of the electrodes on the insulated substrate This allows electrons to be exchanged between the mediator and the electrodes by the supply of a liquid sample, and the target substance in the liquid sample can be measured.

(4)

Also, with the biosensor 2 in the above embodiment, as shown in FIG. 5, in a state in which the reagent component 9 has been disposed on the insulated substrate 4, the thickness d2 of the outer peripheral portion is greater than the thickness d1 of the inner peripheral portion.

(5)

Also, with the biosensor 2 in the above embodiment, as shown in FIG. 5, in a state in which the reagent component 9 has been disposed on the insulated substrate 4, the reagent component 9 is circular in plan view.

(6)

Also, as shown in FIG. 3, the biosensor 2 in the above embodiment comprises the spacer 10 and the cover 11. The spacer 10 is laminated on the side of the insulated substrate 4 where the reagent component 9 is formed. The cover 11 is laminated on the opposite side of the spacer 10 from the insulated substrate 4, and is either transparent or semitransparent. The biological sample introduction path 12 is formed in the spacer 10 (in the portion corresponding to the reagent component 9) to guide biological sample to the reagent component 9.

This allows the biological sample to be drawn up by capillary action into the biological sample introduction path 12 and measured, so the concentration of the target substance can be measured with a small amount of biological sample.

(7)

In the above embodiment, the substance that absorbs light with a wavelength of 400 to 500 nm has a hydrophobic benzene ring portion and a hydrophilic benzene ring portion in its chemical structure formula.

Consequently, when the reagent solution is dried in order to form the reagent component 9, the drying proceeds in a state in which the hydrophobic benzene ring portion appears on the surface side (the cover 11 side), that is, a situation in which this portion rises up to the surface side of the reagent component 9, and as a result, the substance that absorbs light with a wavelength of 400 to 500 nm will be distributed more at the surface portion (the cover 11 side) than in the interior of the reagent component 9. This effectively reduces the effect of light on the mediator with just a small amount of light effect reducing agent.

(8)

In the above embodiment, the substance that absorbs light with a wavelength of 400 to 500 nm is disposed with the hydrophobic benzene ring portion facing the surface layer side of the reagent component. This effectively reduces the effect of light on the mediator with just a small amount of the substance that absorbs light with a wavelength of 400 to 500 nm.

(9)

In the above embodiment, the substance that absorbs light with a wavelength of 400 to 500 nm is Brilliant Blue FCF (Food Blue No. 1), Fast Green FCF (Food Green No. 3), or tartrazine (Food Yellow No. 4). Brilliant Blue FCF (Food Blue No. 1), Fast Green FCF (Food Green No. 3), and tartrazine (Food Yellow No. 4) have a large molar extinction coefficient at a specific wavelength between 400 and 500 nm, and if a mediator with a smaller molar extinction coefficient is used, then the colorant will tend to absorb more light than the mediator, so the effect of light on the mediator can be efficiently reduced.

(10)

In the above embodiment, the reagent component 9 is such that the number of moles of the substance that absorbs light with a wavelength of 400 to 500 nm is less than the number of moles of the mediator. This effectively reduces the effect of light on the mediator with a substance that absorbs light with a wavelength of 400 to 500 nm and that is used in a smaller amount than the mediator.

(11)

In the above embodiment, as shown in FIGS. 13 and 14, the weight ratio of the Fast Green FCF to the entire reagent component 9 is at least 6.01% and no more than 39.02%. This effectively reduces the effect of light on the mediator.

(12)

In the above embodiment, as shown in FIGS. 13 and 15, the weight ratio of the Fast Green FCF to the entire reagent component 9 is at least 11.6% and no more than 116% of the weight ratio of the mediator to the entire reagent component 9. This effectively reduces the effect of light on the mediator.

(13)

In the above embodiment, as shown in FIGS. 13 and 15, the weight ratio of the Brilliant Blue FCF to the entire reagent component 9 is at least 5.9% and no more than 23.87%.

(14)

In the above embodiment, as shown in FIGS. 13 and 15, the weight ratio of the Brilliant Blue FCF to the entire reagent component 9 is at least 11.4% and no more than 56.8% of the weight ratio of the mediator to the entire reagent component 9.

(15)

In the above embodiment, as shown in FIGS. 13 and 16, the weight ratio of the tartrazine to the entire reagent component 9 is at least 4.06% and no more than 29.71%.

(16)

In the above embodiment, as shown in FIGS. 13 and 16, the weight ratio of the tartrazine to the entire reagent component 9 is at least 7.66% and no more than 76.6% of the weight ratio of the mediator to the entire reagent component 9.

(17)

In the above embodiment, the light effect reducing agent is a substance that absorbs light with a wavelength of 400 to 500 nm. This reduces degradation when the mediator absorbs light with a wavelength of 400 to 500 nm.

(18)

In the above embodiment, the method for manufacturing a biosensor comprises a placement step and a drying step. In the placement step, a reagent solution containing at least an oxidoreductase, a mediator, and Fast Green FCF is placed on a first electrode and a second electrode formed on a substrate. In the drying step, the reagent solution thus placed is dried. The concentration of the Fast Green FCF in the reagent solution is at least 1 mM and no more than 10 mM. This reduces degradation when the mediator is exposed to sunlight or the like.

(19)

In the above embodiment, the method for manufacturing a biosensor comprises a placement step and a drying step. In the placement step, a reagent solution containing at least an oxidoreductase, a mediator, and Brilliant Blue FCF is placed on a first electrode and a second electrode formed on a substrate. In the drying step, the reagent solution thus placed is dried. The concentration of the Brilliant Blue FCF in the reagent solution is at least 1 mM and no more than 5 mM. This reduces degradation when the mediator is exposed to sunlight or the like.

(20)

In the above embodiment, the method for manufacturing a biosensor comprises a placement step and a drying step. In the placement step, a reagent solution containing at least an oxidoreductase, a mediator, and tartrazine is placed on a first electrode and a second electrode formed on a substrate. In the drying step, the reagent solution thus placed is dried. The concentration of the tartrazine in the reagent solution is at least 1 mM and no more than 10 mM. This reduces degradation when the mediator is exposed to sunlight or the like.

Other Embodiments (A)

In the above embodiment, PQSA was used as an example of a mediator, but this is not the only option, and some other mediator may be used instead.

FIGS. 17a, 17b, and 17c are graphs of the absorption spectra of potassium ferricyanide, ferrocenylmethyl dodecyl dimethyl ammonium bromide, and hexachloro-oxamate are used as mediators.

As shown in FIGS. 17a to 17c, potassium ferricyanide, ferrocenylmethyl dodecyl dimethyl ammonium bromide, and hexachloro-oxamate absorb light with a wavelength of 400 to 500 nm, and are therefore susceptible being affected by sunlight exposure.

Therefore, when these mediators are used, the light effect reducing agent in this embodiment can be used to reduce the effect that sunlight exposure has on measurement values. Specifically, the light effect reducing agent of the present invention exhibits a better effect when using a mediator that absorbs light with a wavelength of 400 to 500 nm.

(B)

The composition of the reagent in the present invention is not limited to the composition used in the above embodiment. For example, in the above embodiment $HPO_4$, $KH_2PO_4$, and $NaH_2PO_4$ were used as buffers, but this is not the only option, and HEPES or another such buffer may be used instead.

INDUSTRIAL APPLICABILITY

As discussed above, with the present invention, various biosensors can be made less susceptible to the effect of light, and as a result degradation of the biosensors can be reduced. Therefore, the present invention is expected to find application as a biosensor for sensing blood glucose levels and other such biological information.

REFERENCE SIGNS LIST 1 main case
2 biosensor
3 insertion slot
4 insulated substrate (an example of a substrate)
5 blood component measurement working electrode (an example of a first electrode)
6 blood component measurement counter electrode (an example of a second electrode)
7 blood component detection electrode
8 input terminal component
9 reagent component
11 cover
10 spacer
12 biological sample introduction path
13 blood supply opening
15 voltage application component
16 current-voltage converter
17 switching circuit
18 applied voltage part
19 reference voltage part
20 power supply
21 controller
22 A/D converter
23 determination means
25 memory
26 clock
27 correction means

The invention claimed is:

1. A biosensor, comprising:
a first electrode;
a second electrode; and
a reagent component that is provided near the first electrode and the second electrode,
wherein the reagent component includes:
  a mediator;
  an oxidoreductase; and
  Fast Green FCF that absorbs light with a wavelength of 400 to 500 nm, and
the Fast Green FCF is present in the reagent component in a weight ratio of at least 6.01% and no more than 39.02%.

2. The biosensor according to claim 1, comprising:
a substrate, the first electrode and/or the second electrode being disposed on a surface thereof,
wherein the reagent component is disposed on one or both of the first electrode and the second electrode on the substrate.

3. The biosensor according to claim 2,
wherein the reagent component is formed such that an outer peripheral portion is thicker than an inner portion on the substrate.

4. The biosensor according to claim 3,
wherein the reagent component has a circular shape in plan view on the substrate.

5. The biosensor according to claim 2, comprising:
a spacer laminated on a side of the substrate where the reagent component is formed; and
a transparent or semitransparent cover laminated on an opposite side of the spacer from the substrate,
wherein a biological sample introduction component that guides a biological sample to a portion corresponding to the reagent component is formed in the spacer.

6. The biosensor according to claim 1,
wherein the Fast Green FCF that absorbs light with a wavelength of 400 to 500 nm is disposed with a hydrophobic benzene ring portion facing a surface layer side of the reagent component.

7. The biosensor according to claim 1,
wherein the number of moles of the Fast Green FCF that absorbs light with a wavelength of 400 to 500 nm is less than the number of moles of the mediator.

8. The biosensor according to claim 1,
wherein the ratio of the number of moles of Fast Green FCF to the number of moles of the mediator is at least 0.0442 and no more than 0.422.

9. A biosensor, comprising:
a first electrode;
a second electrode; and
a reagent component that is provided near the first electrode and the second electrode,
wherein the reagent component includes:
  a mediator;
  an oxidoreductase; and
  Brilliant Blue FCF that absorbs light with a wavelength of 400 to 500 nm, and
the Brilliant Blue FCF is present in the reagent component in a weight ratio of at least 5.9% and no more than 23.87%.

10. The biosensor according to claim 9,
wherein the ratio of the number of moles of the Brilliant Blue FCF to the number of moles of the mediator is at least 0.0442 and no more than 0.221.

11. The biosensor according to claim 9, comprising:
a substrate, the first electrode, and/or the second electrode being disposed on a surface thereof, wherein the reagent component is disposed on one or both of the first electrode and the second electrode on the substrate.

12. The biosensor according to claim 11,
wherein the reagent component is formed such that an outer peripheral portion is thicker than an inner portion on the substrate.

13. The biosensor according to claim 12,
wherein the reagent component has a circular shape in plan view on the substrate.

14. The biosensor according to claim 11 comprising:
a spacer laminated on a side of the substrate where the reagent component is formed; and
a transparent or semitransparent cover laminated on an opposite side of the spacer from the substrate,
wherein a biological sample introduction component that guides a biological sample to a portion corresponding to the reagent component is formed in the spacer.

15. The biosensor according to claim 9,
wherein the Brilliant Blue FCF that absorbs light with a wavelength of 400 to 500 nm is disposed with a hydrophobic benzene ring portion facing a surface layer side of the reagent component.

16. The biosensor according to claim 9,
wherein the number of moles of the Brilliant Blue FCF that absorbs light with a wavelength of 400 to 500 nm is less than the number of moles of the mediator.

* * * * *